(12) United States Patent
Nojiri et al.

(10) Patent No.: US 11,452,674 B2
(45) Date of Patent: Sep. 27, 2022

(54) NON-SOLVENT DENTAL ADHESIVE COMPOSITION

(71) Applicant: KURARAY NORITAKE DENTAL INC., Kurashiki (JP)

(72) Inventors: Yamato Nojiri, Niigata (JP); Mitsunobu Kawashima, Niigata (JP); Ryo Matsuura, Niigata (JP); Ryota Murayama, Niigata (JP)

(73) Assignee: KURARAY NORITAKE DENTAL INC., Kurashiki (JP)

( * ) Notice: Subject to any disclaimer, the term of this patent is extended or adjusted under 35 U.S.C. 154(b) by 324 days.

(21) Appl. No.: 16/642,708

(22) PCT Filed: Aug. 28, 2018

(86) PCT No.: PCT/JP2018/031734
§ 371 (c)(1),
(2) Date: Feb. 27, 2020

(87) PCT Pub. No.: WO2019/044815
PCT Pub. Date: Mar. 7, 2019

(65) Prior Publication Data
US 2020/0206091 A1    Jul. 2, 2020

(30) Foreign Application Priority Data

Aug. 28, 2017 (JP) .............................. JP2017-163722

(51) Int. Cl.
| | | |
|---|---|---|
| *A61K 6/30* | (2020.01) | |
| *C08F 2/50* | (2006.01) | |
| *C08F 220/20* | (2006.01) | |
| *C08F 220/56* | (2006.01) | |
| *C08F 230/02* | (2006.01) | |
| *C08F 236/02* | (2006.01) | |
| *C08K 3/36* | (2006.01) | |
| *C08K 3/40* | (2006.01) | |
| *C08K 5/18* | (2006.01) | |
| *C08K 5/5313* | (2006.01) | |
| *C08K 5/5317* | (2006.01) | |
| *C08K 9/06* | (2006.01) | |

(52) U.S. Cl.
CPC ................. *A61K 6/30* (2020.01); *C08F 2/50* (2013.01); *C08F 220/20* (2013.01); *C08F 220/56* (2013.01); *C08F 230/02* (2013.01); *C08F 236/02* (2013.01); *C08K 3/36* (2013.01); *C08K 3/40* (2013.01); *C08K 5/18* (2013.01); *C08K 5/5313* (2013.01); *C08K 5/5317* (2013.01); *C08K 9/06* (2013.01); *C08K 2201/003* (2013.01)

(58) Field of Classification Search
CPC . A61K 6/30; C08F 2/50; C08F 220/20; C08F 220/56; C08F 236/02; C08K 3/36; C08K 3/40; C08K 4/18; C08K 4/5513; C08K 4/5317; C08K 9/02; C08K 2201/003
See application file for complete search history.

(56) References Cited

U.S. PATENT DOCUMENTS

| | | |
|---|---|---|
| 4,719,297 A | 1/1988 | Henne et al. |
| 6,355,704 B1 | 3/2002 | Nakatsuka et al. |
| 2010/0048762 A1 | 2/2010 | Ishino et al. |
| 2010/0130682 A1 | 5/2010 | Hinamoto et al. |
| 2011/0124763 A1 | 5/2011 | Hinamoto et al. |
| 2017/0065496 A1 | 3/2017 | Boettcher et al. |

FOREIGN PATENT DOCUMENTS

| | | |
|---|---|---|
| CA | 2 926 060 A1 | 4/2015 |
| CA | 2 962 606 A1 | 3/2016 |
| JP | 57-197289 A | 12/1982 |
| JP | 9-003109 A | 1/1997 |
| JP | 10-245525 A | 9/1998 |
| JP | 2000-16911 A | 1/2000 |
| JP | 2000-159621 A | 6/2000 |
| JP | 2000-212015 A | 8/2000 |
| JP | 2005-248137 A | 9/2005 |
| JP | 2012-46456 A | 3/2012 |
| JP | 2012-62280 A | 3/2012 |
| WO | WO 2008/087977 A1 | 7/2008 |
| WO | WO 2008/087981 A1 | 7/2008 |
| WO | WO 2010/008077 A1 | 1/2010 |
| WO | WO 2014/095724 A1 | 6/2014 |

OTHER PUBLICATIONS

Extended European Search Report dated Mar. 4, 2021 in European Patenet Application No. 18851544.9, 8 pages.
Benedikt, S., et al., "Highly Efficient Water-Soluble Visible Light Photoinitiators", Journal of Polymer Science Part A: Polymer Chemistry, vol. 54, No. 4, Feb. 15, 2016, XP055718910, pp. 473-479.
Nagi, S.M., "Durability of solvent-free one-step self-etch adhesive under simulated intrapulpal pressure", Journal of Clinical and Experimental Dentistry, Retrieved from the internet: URL:http://www.medicinaoral.com/odo/volumenes/v714/jcedy714p466.pdf, Jan. 1, 2015, XP055779414, pp. e466-e470.

(Continued)

Primary Examiner — Edward J Cain
(74) Attorney, Agent, or Firm — Oblon, McClelland, Maier & Neustadt, L.L.P.

(57) ABSTRACT

The present invention provides a non-solvent dental adhesive composition exhibiting high initial bond strength and high bond durability to a tooth structure (wet matter) and a high dentin cohesive failure rate on a tooth structure (wet matter) and being substantially free of water and an organic solvent. The present invention relates to a non-solvent dental adhesive composition comprising: an acid group-containing polymerizable monomer (A); a hydrophobic polymerizable monomer (B) having no acid group; and a water-soluble photopolymerization initiator (C) having a solubility of 10 g/L or more in water at 25° C.

11 Claims, No Drawings

(56) References Cited

OTHER PUBLICATIONS

Canadian Office Action dated Apr. 15, 2021 in Canadian Patent Application No. 3,074,195, 4 pages.
Moszner, N. et al., "Chemical aspects of self-etching enamel-dentin adhesives: A systematic review," dental materials, vol. 21, 2005, pp. 895-910.
International Search Report dated Oct. 9, 2018 in PCT/JP2018/031734 filed on Aug. 28, 2018, 1 page.

NON-SOLVENT DENTAL ADHESIVE COMPOSITION

TECHNICAL FIELD

The present invention relates to a dental adhesive composition used in the field of dentistry. More specifically, the present invention relates to a non-solvent dental adhesive composition which is substantially free of water and an organic solvent and curing of which is promoted at an adhesive interface by contact with a moisture-containing wet matter.

BACKGROUND ART

A restorative filling material such as a filling composite resin or a filling compomer or a crown restoration material such as a metal alloy, a porcelain, or a resin material is typically used for restoration of tooth structures (enamel, dentin, and cementum) damaged, for example, by dental caries. In general, however, restorative filling materials and crown restoration materials (both of these materials may collectively be referred to as "dental restorative material(s)" in the present specification) themselves have no adhesiveness to tooth structures. This is why bonding between tooth structures and dental restorative materials conventionally employs various adhesive systems involving the use of adhesives. An example of conventionally-employed adhesive systems is an adhesive system of the so-called acid etching type (total etching type), the use of which consists of subjecting the surface of a tooth structure to an etching treatment with an acid etching agent such as an aqueous phosphoric acid solution, then applying a bonding material which is an adhesive to the tooth structure, and bonding a dental restorative material to the tooth structure.

Meanwhile, there are adhesive systems of the so-called self-etching type, which involve no use of any acid etching agent. A conventionally dominant adhesive system of this type is a two-step adhesive system, the use of which consists of applying a self-etching primer containing an acidic monomer, a hydrophilic monomer, and water to the surface of a tooth structure and then, without washing with water, applying a bonding material containing a crosslinkable monomer and a polymerization initiator to the tooth structure. Recently, a one-step adhesive system involving the use of a one-pack dental adhesive (one-pack bonding material) having functions of both a self-etching primer and a bonding material has been widely employed.

An acidic monomer, a hydrophilic monomer, a crosslinkable monomer, and the like are commonly contained as monomer components in a one-pack bonding material, and water or a hydrophilic volatile organic solvent is commonly used for a one-pack bonding material.

However, when a one-pack bonding material as described above is used to restore a cavity, water and an organic solvent contained in the bonding material needs to be removed by air-blowing before curing of the one-pack bonding material. This is because the presence of water or an organic solvent causes insufficient curing or delay in curing. Therefore, a demand for a non-solvent dental adhesive composition substantially free of water and an organic solvent has been increasing in order to omit a step, for example, of air-blowing for removing water and an organic solvent.

Recently, self-adhesive dental composite resins which are dental composite resins having adhesiveness have been developed, and non-solvent dental adhesive compositions usable for restorative treatment with fewer steps and without the use of a bonding material have also begun to be used practically.

In both of the above-described adhesion systems, it is common to apply a bonding material to a portion to be restored and cause photocuring of the bonding material. In the case of a self-adhesive dental composite resin, it is common to pour a self-adhesive dental composite resin in a portion to be restored and cause photocuring of the self-adhesive dental composite resin. Therefore, a photopolymerization initiator is used in these adhesion systems to impart the photopolymerizability. Camphorquinone/a tertiary amine, which are conventionally well-known photopolymerization initiators, are the most common as such a photopolymerization initiator. Acylphosphine oxide compounds are known as photopolymerization initiators having excellent photocurability and being less likely to cause a color change and coloring. In particular, 2,4,6-trimethylbenzoyldiphenylphosphine oxide is known to impart excellent adhesiveness to tooth structures to a polymerizable composition and is widely used (see Non Patent Literature 1).

Patent Literatures 1 to 3, for example, also propose two-step and one-step adhesion systems which involve inclusion of an acylphosphine oxide compound. However, when the amount of such a conventional acylphosphine oxide compound serving as a photopolymerization initiator is increased with an aim to improve the curability at an adhesive interface for further improvement of the adhesiveness, the curability of the resulting composition itself is increased but improvement of the adhesiveness to a tooth structure is limited. Moreover, such a conventional acylphosphine oxide compound has a low solubility in water and is thus insufficiently dissolved, dispersed, and diffused in a tooth structure which is a wet matter. A study later carried out by the present inventors has revealed room for improvement.

Patent Literature 4 describes a dental photopolymerizable composition containing, as main constituent elements, a (meth)acrylate monomer, water, and a water-soluble acylphosphine oxide compound serving as a photopolymerization initiator. However, water is an essential component of the composition according to Patent Literature 4, and thus employment of the composition according to Patent Literature 4 as a non-solvent dental adhesive composition substantially free of water and an organic solvent is difficult, which fact has been known since the disclosure thereof.

Patent Literatures 5 and 6 propose polymerizable compositions capable of imparting high adhesiveness to tooth structures and containing a novel (bis)acylphosphine oxide compound capable of imparting stable adhesiveness which varies little according to adhesion operations. However, it has been confirmed that employment of these polymerizable compositions as non-solvent dental adhesive compositions substantially free of water and an organic solvent has problems in that polymerization at an adhesive interface is not promoted sufficiently, that both the initial bond strength and the bond durability to dentin are low, and that while failure caused in an adhesion test is cohesive failure of dentin serving as an adherend in the case where the adhesiveness is sufficiently high, failure at the interface between each adhesive composition and dentin is dominant due to poor bond strength. A study later carried out by the present inventors has revealed room for improvement.

CITATION LIST

Patent Literature

Patent Literature 1: JP 2000-16911 A
Patent Literature 2: JP 2000-212015 A

Patent Literature 3: WO 2010/008077 A1
Patent Literature 4: JP 2000-159621 A
Patent Literature 5: JP 2012-46456 A
Patent Literature 6: JP 2012-62280 A Non Patent Literature Non Patent Literature 1: Dental Materials, 2005, volume 21, pp. 895 to 910

SUMMARY OF INVENTION

Technical Problem

It is therefore an object of the present invention to provide a non-solvent dental adhesive composition exhibiting high initial bond strength and high bond durability to a tooth structure (wet matter) and a high dentin cohesive failure rate on a tooth structure (wet matter) and being substantially free of water and an organic solvent.

Solution to Problem

As a result of intensive studies, the present inventors have found that the above disadvantages can be solved by a non-solvent dental adhesive composition comprising a certain photopolymerization initiator, and have completed the present invention based on this finding.

That is, the present invention includes the following.

[1] A non-solvent dental adhesive composition comprising: an acid group-containing polymerizable monomer (A); a hydrophobic polymerizable monomer (B) having no acid group; and a water-soluble photopolymerization initiator (C) having a solubility of 10 g/L or more in water at 25° C.

[2] The non-solvent dental adhesive composition according to [1], further comprising a hydrophilic polymerizable monomer (D) having no acid group.

[3] The non-solvent dental adhesive composition according to [2], wherein the content of the hydrophilic polymerizable monomer (D) having no acid group with respect to the total mass of the hydrophobic polymerizable monomer (B) having no acid group and the hydrophilic polymerizable monomer (D) having no acid group is 50 mass % or less.

[4] The non-solvent dental adhesive composition according to any one of [1] to [3], wherein the water-soluble photopolymerization initiator (C) is at least one selected from the group consisting of a compound represented by a general formula (1) and a compound represented by a general formula (2):

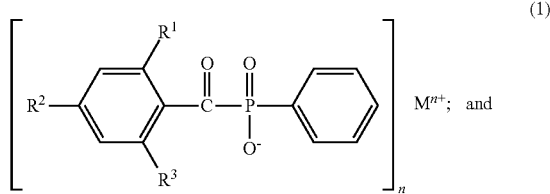

$M^{n+}$; and

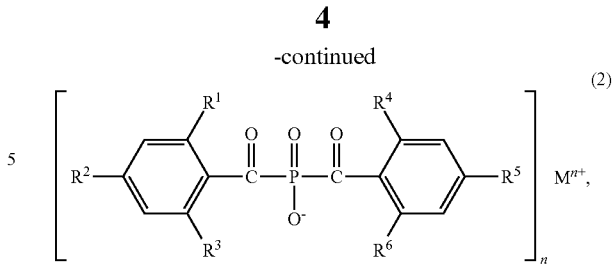

wherein $R^1$, $R^2$, $R^3$, $R^4$, $R^5$, and $R^6$ are each independently a linear or branched alkyl group having 1 to 4 carbon atoms or a halogen atom; M is hydrogen ion, alkali metal ion, alkaline-earth metal ion, magnesium ion, pyridinium ion having an optionally substituted pyridine ring, or ammonium ion expressed by $HN^+R^7R^8R^9$, wherein $R^7$, $R^8$, and $R^9$ are each independently an organic group or a hydrogen atom; and n represents 1 or 2.

[5] The non-solvent dental adhesive composition according to any one of [1] to [4], wherein the acid group-containing polymerizable monomer (A) is a phosphate group-containing polymerizable monomer.

[6] The non-solvent dental adhesive composition according to any one of [1] to [5], further comprising a water-insoluble photopolymerization initiator (E) having a solubility of less than 10 g/L in water at 25° C.

[7] The non-solvent dental adhesive composition according to [6], wherein the mass ratio between the water-soluble photopolymerization initiator (C) and the water-insoluble photopolymerization initiator (E) is 10:1 to 1:10.

[8] A dental bonding material comprising the non-solvent dental adhesive composition according to any one of [1] to [7].

[9] A self-adhesive dental composite resin comprising the non-solvent dental adhesive composition according to [1] to [7].

[10] A dental cement comprising the non-solvent dental adhesive composition according to any one of [1] to [7].

Advantageous Effects of Invention

The present invention provides a non-solvent dental adhesive composition exhibiting high initial bond strength and high bond durability to a tooth structure (wet matter) and a high dentin cohesive failure rate on a tooth structure (wet matter) and being substantially free of water and an organic solvent; and a dental bonding material, a self-adhesive dental composite resin, and a dental cement for which the composition is used.

The present invention further provides a non-solvent dental adhesive composition exhibiting high initial bond strength and high bond durability also to a tooth structure in dry condition and a high dentin cohesive failure rate also on a tooth structure in dry condition by compositionally adjusting a hydrophobic polymerizable monomer and a hydrophilic polymerizable monomer. As described above, a tooth structure is a wet matter, and dentin, in particular, contains 12% water. Although dried by air-blowing after cutting with an air turbine under water injection and washing with water, the surface of a tooth to be restored is generally in wet condition due to the influence of highly humid expired air. The above-described compositional adjustment leads to exhibition of high initial bond strength, high bond durability, and a high dentin cohesive failure rate even in dry condition created by setting a moisture preventing device such as a rubber dam to block the influence of expired air on a tooth to be restored and removing water on the surface of the tooth by air-blowing. It should be added that in the present specification, a tooth structure (or dentin) in "dry condition" refers to one in a condition where water on the surface thereof is sufficiently removed by air-blowing.

DESCRIPTION OF EMBODIMENTS

The non-solvent dental adhesive composition of the present invention comprises an acid group-containing polymerizable monomer (A), a hydrophobic polymerizable monomer (B) having no acid group, and a water-soluble photopolymerization initiator (C) having a solubility of 10 g/L or more in water at 25° C. (hereinafter simply referred to as "water-soluble photopolymerization initiator (C)") as essential components. The term "(meth)acrylate" as used in the present specification collectively refers to acrylate and methacrylate. The same applies to similar expressions. In the present specification, the upper limits and lower limits of value ranges (ranges of, for example, the contents of components, values calculated for components, and values of physical properties) can be combined appropriately.

Because the non-solvent dental adhesive composition of the present invention is free of a solvent, namely, water and an organic solvent, that causes insufficient curing or delay in curing, the non-solvent dental adhesive composition of the present invention has advantages in that a solvent removal step, for example, involving air-blowing can be omitted from curing of the non-solvent dental adhesive composition and in that the non-solvent dental adhesive composition can be applied to a self-adhesive dental composite resin that is a dental composite resin being free of water and an organic solvent and having adhesiveness. It should be added that as long as no trouble such as insufficient curing or delay in curing is caused, a small amount (for example, 3 mass % or less with respect to the composition) of moisture or an organic solvent may be incorporated. Some commercially available components (for example, colloidal silica) to be contained contain water or an organic solvent. From such components are removed water and the organic solvent so that the total amount thereof will be within the allowable limit. The components are thereafter used to prepare the non-solvent dental adhesive composition of the present invention.

It is not known exactly why the non-solvent dental adhesive composition of the present invention exhibits high initial bond strength and high bond durability to dentin and a high dentin cohesive failure rate on dentin. The reason for this is probably as follows. That is, this is attributable to the fact that the polymerization curability at a hydrophilic tooth structure interface is improved by comprising the water-soluble photopolymerization initiator (C). A tooth structure, particularly dentin, contains moisture, and the interface thereof is thus hydrophilic. In order to increase the bond strength to dentin, a resin-impregnated layer into which a polymerizable monomer of a dental adhesive composition penetrates needs to be formed at the hydrophilic tooth structure interface and the rate of polymerization needs to be increased to obtain a strong adhesive layer. A non-solvent dental adhesive composition, such as a conventional self-adhesive dental composite resin, which is free of a solvent has weak demineralization ability and weak penetration ability. A composition for which an ordinary water-insoluble photopolymerization initiator is used has an insufficient rate of polymerization and gives a weak resin-impregnated layer. Therefore, to compensate for the shortcoming and form a desirable resin-impregnated layer, the polymerization curability of the adhesive interface portion and that of the inside of the resin-impregnated layer particularly need to be increased. In contrast, since the water-soluble photopolymerization initiator (C) is used for the non-solvent dental adhesive composition of the present invention, the concentration of the water-soluble photopolymerization initiator (C) is high at a portion where the water-soluble photopolymerization initiator (C) is in contact with the surface of a tooth structure (wet matter) and locally dissolved in water, and the polymerization curability of the adhesive interface portion and that of the inside of the resin-impregnated layer can be selectively increased. It is thought that the non-solvent dental adhesive composition of the present invention therefore has high bond strength.

The components used in the non-solvent dental adhesive composition of the present invention will be described hereinafter.

[Acid Group-Containing Polymerizable Monomer (A)]

The acid group-containing polymerizable monomer (A) is a component that has acid-etching effect and priming effect and imparts demineralization ability and penetration ability. The acid group-containing polymerizable monomer (A) is capable of polymerization and imparts curing ability. The inclusion of the acid group-containing polymerizable monomer (A) can contribute to enhancement of adhesiveness and bond durability to tooth structures.

An example of the acid group-containing polymerizable monomer (A) is a polymerizable monomer having at least one of acid groups such as a phosphoric acid group, a pyrophosphoric acid group, a thiophosphoric acid group, a phosphonic acid group, a sulfonic acid group, and a carboxylic acid group and having at least one of polymerizable groups such as an acryloyl group, a methacryloyl group, a vinyl group, and a styrene group. Specific examples of the acid group-containing polymerizable monomer (A) are presented below.

Examples of the phosphoric acid group-containing polymerizable monomer include: 2-(meth)acryloyloxyethyl dihydrogen phosphate, 3-(meth)acryloyloxypropyl dihydrogen phosphate, 4-(meth)acryloyloxybutyl dihydrogen phosphate, 5-(meth)acryloyloxypentyl dihydrogen phosphate, 6-(meth)acryloyloxyhexyl dihydrogen phosphate, 7-(meth)acryloyloxyheptyl dihydrogen phosphate, 8-(meth)acryloyloxyoctyl dihydrogen phosphate, 9-(meth)acryloyloxynonyl dihydrogen phosphate, 10-(meth)acryloyloxydecyl dihydrogen phosphate, 11-(meth)acryloyloxyundecyl dihydrogen phosphate, 12-(meth)acryloyloxydodecyl dihydrogen phosphate, 16-(meth)acryloyloxyhexadecyl dihydrogen phosphate, 20-(meth)acryloyloxyicosyl dihydrogen phosphate, bis[2-(meth)acryloyloxyethyl] hydrogen phosphate, bis[4-(meth)acryloyloxybutyl] hydrogen phosphate, bis[6-(meth)acryloyloxyhexyl] hydrogen phosphate, bis[8-(meth)acryloyloxyoctyl] hydrogen phosphate, bis[9-(meth)acryloyloxynonyl] hydrogen phosphate, bis[10-(meth)acryloyloxydecyl] hydrogen phosphate, 1,3-di(meth)acryloyloxypropyl dihydrogen phosphate, 2-(meth)acryloyloxyethylphenyl hydrogen phosphate, 2-(meth)acryloyloxyethyl-2-bromoethyl hydrogen phosphate, and bis[2-(meth)acryloyloxy-(1-hydroxymethyl)ethyl] hydrogen phosphate; and their acid chlorides, alkali metal salts, and ammonium salts.

Examples of the pyrophosphoric acid group-containing polymerizable monomer include: bis[2-(meth)acryloyloxyethyl] pyrophosphate, bis[4-(meth)acryloyloxybutyl] pyrophosphate, bis[6-(meth)acryloyloxyhexyl] pyrophosphate, bis[8-(meth)acryloyloxyoctyl] pyrophosphate, and bis[10-(meth)acryloyloxydecyl] pyrophosphate; and their acid chlorides, alkali metal salts, and ammonium salts.

Examples of the thiophosphoric acid group-containing polymerizable monomer include: 2-(meth)acryloyloxyethyl dihydrogen thiophosphate, 3-(meth)acryloyloxypropyl dihydrogen thiophosphate, 4-(meth)acryloyloxybutyl dihydrogen thiophosphate, 5-(meth)acryloyloxypentyl dihydrogen thiophosphate, 6-(meth)acryloyloxyhexyl dihydrogen thiophosphate, 7-(meth)acryloyloxyheptyl dihydrogen thiophosphate, 8-(meth)acryloyloxyoctyl dihydrogen thiophosphate, 9-(meth)acryloyloxynonyl dihydrogen thiophosphate, 10-(meth)acryloyloxydecyl dihydrogen thiophosphate, 11-(meth)acryloyloxyundecyl dihydrogen thiophosphate, 12-(meth)acryloyloxydodecyl dihydrogen thiophosphate, 16-(meth)acryloyloxyhexadecyl dihydrogen thiophosphate, and 20-(meth)acryloyloxyicosyl dihydrogen thiophosphate; and their acid chlorides, alkali metal salts, and ammonium salts.

Examples of the phosphonic acid group-containing polymerizable monomer include: 2-(meth)acryloyloxyethylphenyl phosphonate, 5-(meth)acryloyloxypentyl-3-phosphonopropionate, 6-(meth)acryloyloxyhexyl-3-phosphonopropionate, 10-(meth)acryloyloxydecyl-3-phosphonopropionate, 6-(meth)acryloyloxyhexyl-3-phosphonoacetate, and 10-(meth)acryloyloxydecyl-3-phosphonoacetate; and their acid chlorides, alkali metal salts, and ammonium salts.

Examples of the sulfonic acid group-containing polymerizable monomer include 2-(meth)acrylamido-2-methylpropanesulfonic acid, styrenesulfonic acid, and 2-sulfoethyl (meth)acrylate.

Examples of the carboxylic acid group-containing polymerizable monomer include a polymerizable monomer having one carboxy group per molecule and a polymerizable monomer having two or more carboxy groups per molecule.

Examples of the polymerizable monomer having one carboxy group per molecule include (meth)acrylic acid, N-(meth)acryloylglycine, N-(meth)acryloylaspartic acid, O-(meth)acryloyltyrosine, N-(meth)acryloyltyrosine, N-(meth)acryloylphenylalanine, N-(meth)acryloyl-p-aminobenzoic acid, N-(meth)acryloyl-o-aminobenzoic acid, p-vinylbenzoic acid, 2-(meth)acryloyloxybenzoic acid, 3-(meth)acryloyloxybenzoic acid, 4-(meth)acryloyloxybenzoic acid, N-(meth)acryloyl-5-aminosalicylic acid, N-(meth)acryloyl-4-aminosalicylic acid, 2-(meth)acryloyloxyethyl hydrogen succinate, 2-(meth)acryloyloxyethyl hydrogen phthalate, 2-(meth)acryloyloxyethyl hydrogen malate, and their acid halides.

Examples of the polymerizable monomer having two or more carboxy groups per molecule include: 6-(meth)acryloyloxyhexane-1,1-dicarboxylic acid, 9-(meth)acryloyloxynonane-1,1-dicarboxylic acid, 10-(meth)acryloyloxydecane-1,1-dicarboxylic acid, 11-(meth)acryloyloxyundecane-1,1-dicarboxylic acid, 12-(meth)acryloyloxydodecane-1,1-dicarboxylic acid, 13-(meth)acryloyloxytridecane-1,1-dicarboxylic acid, 4-(meth)acryloyloxyethyl trimellitate, 4-(meth)acryloyloxyethyl trimellitate anhydride, 4-(meth)acryloyloxybutyl trimellitate, 4-(meth)acryloyloxyhexyl trimellitate, 4-(meth)acryloyloxydecyl trimellitate, and 2-(meth)acryloyloxyethyl-3'-(meth)acryloyloxy-2'-(3,4-dicarboxybenzoyloxy)propyl succinate; and their acid anhydrides and acid halides.

Among these acid group-containing polymerizable monomers, the phosphoric or pyrophosphoric acid group-containing (meth)acrylic monomers are preferred since such monomers provide better adhesiveness to tooth structures. Particularly preferred are the phosphoric acid group-containing (meth)acrylic monomers. Among the phosphoric acid group-containing (meth)acrylic monomers, a divalent phosphoric acid group-containing (meth)acrylic monomer that has as the main chain of the molecule an alkyl or alkylene group having 6 to 20 carbon atoms is more preferred, and a divalent phosphoric acid group-containing (meth)acrylic monomer that has as the main chain of the molecule an alkylene group having 8 to 12 carbon atoms, such as 10-methacryloyloxydecyl dihydrogen phosphate, is most preferred, in terms of exhibiting high demineralization ability in the absence of an organic solvent and exhibiting high adhesiveness.

One monomer may be used alone as the acid group-containing polymerizable monomer (A) or a combination of two or more monomers may be used as the acid group-containing polymerizable monomers (A). Having too high or low a content of the acid group-containing polymerizable monomer (A) may cause a decline in adhesiveness. Thus, the content of the acid group-containing polymerizable monomer (A) is preferably in the range of 1 to 50 parts by mass, more preferably in the range of 3 to 40 parts by mass, and most preferably in the range of 5 to 30 parts by mass, with respect to 100 parts by mass of the total polymerizable monomer components in the non-solvent dental adhesive composition.

[Hydrophobic Polymerizable Monomer (B) having no Acid Group]

As the hydrophobic polymerizable monomer (B) having no acid group, radical polymerizable monomers having no acid group and having a polymerizable group are preferred. The polymerizable group is preferably a (meth)acryl group and/or a (meth)acrylamide group in terms of ease of radical polymerization. The hydrophobic polymerizable monomer (B) having no acid group refers to a polymerizable monomer having no acid group and having a solubility of less than 10 weight % in water at 25° C. Examples of the hydrophobic polymerizable monomer (B) having no acid group include crosslinkable polymerizable monomers such as difunctional aromatic polymerizable monomers, difunctional aliphatic polymerizable monomers, and tri- or higher-functional polymerizable monomers. The hydrophobic polymerizable monomer (B) having no acid group improves the characteristics such as mechanical strength and handling properties of the non-solvent dental adhesive composition.

Examples of the difunctional aromatic polymerizable monomer include 2,2-bis((meth)acryloyloxyphenyl)propane, 2,2-bis[4-(3-(meth)acryloyloxy-2-hydroxypropoxy)phenyl]propane, 2,2-bis(4-(meth)acryloyloxyethoxyphenyl)propane, 2,2-bis(4-(meth)acryloyloxypolyethoxyphenyppropane, 2,2-bis(4-(meth)acryloyloxydiethoxyphenyl)propane, 2,2-bis(4-(meth)acryloyloxytriethoxyphenyl)propane, 2,2-bis(4-(meth)acryloyloxytetraethoxyphenyl)propane, 2,2-bis(4-(meth)acryloyloxypentaethoxyphenyl)propane, 2,2-bis(4-(meth)acryloyloxydipropoxyphenyl)propane, 2-(4-(meth)acryloyloxydiethoxyphenyl)-2-(4-(meth)acryloyloxyethoxyphenyl)propane, 2-(4-(meth)acryloyloxydiethoxyphenyl)-2-(4-(meth)acryloyloxytriethoxyphenyppropane, 2-(4-(meth)acryloyloxydipropoxyphenyl-2-(4-(meth)acryloyloxytriethoxyphenyl)propane, 2,2-bis(4-(meth)acryloyloxypropoxyphenyl)propane, and 2,2-bis(4-(meth)acryloyloxyisopropoxyphenyl)propane. Preferred among these are 2,2-bis[4-(3-methacryloyloxy-2-hydroxypropoxy)phenyl]propane (commonly known as "Bis-GMA"), 2,2-bis(4-(meth)acryloyloxyethoxyphenyl)propane, 2,2-bis(4-methacryloyloxypolyethoxyphenyl)propane (having an average number of moles of added ethoxy groups of 2.6, commonly known as "D-2.6E"), 2,2-bis(4-(meth)acryloyloxydiethoxyphenyl)propane, 2,2-bis(4-(meth)acryloyloxytriethoxyphenyl)propane, 2,2-bis(4-(meth)acryloyloxytetraethoxyphenyl)propane, and 2,2-bis(4-(meth)acryloyloxypentaethoxyphenyl)propane.

Examples of the difunctional aliphatic polymerizable monomers include: glycerol di(meth)acrylate, ethylene glycol di(meth)acrylate, diethylene glycol di(meth)acrylate, triethylene glycol di(meth)acrylate, propylene glycol di(meth)acrylate, butylene glycol di(meth)acrylate, neopentyl glycol di(meth)acrylate, 1,3-butanediol di(meth)acrylate, 1,5-pentanediol di(meth)acrylate, 1,6-hexanediol di(meth)acrylate, 1,10-decanediol di(meth)acrylate, 1,2-bis(3-methacryloyloxy-2-hydroxypropoxy)ethane, 2,2,4-trimethylhexamethylenebis(2-carbamoyloxyethyl) di(meth)acrylate, N-methacryloyloxyethyl acrylamide, and N-methacryloyloxypropyl amide. Among these, triethylene glycol diacrylate, triethylene glycol dimethacrylate (commonly known as "3G"), neopentyl glycol di(meth)acrylate, 1,2-bis(3-methacryloyloxy-2-hydroxypropoxy)ethane, and 2,2,4-trimethylhexamethylenebis(2-carbamoyloxyethyl) dimethacrylate (commonly known as "UDMA") are preferred. To exhibit high initial bond strength and high bond durability also to a tooth structure in dry condition and a high dentin cohesive failure rate also on a tooth structure in dry condition, 1,10-decanediol dimethacrylate (commonly known as "DD"), 2,2,4-trimethylhexamethylenebis(2-carbamoyloxyethyl) dimethacrylate, and N-methacryloyloxyethyl acrylamide (commonly known as "MAEA") are preferred.

Examples of the tri- or higher-functional polymerizable monomers include trimethylolpropane tri(meth)acrylate, trimethylolethane tri(meth)acrylate, trimethylolmethane tri(meth)acrylate, pentaerythritol tri(meth)acrylate, pentaerythritol tetra(meth)acrylate, dipentaerythritol penta(meth)acrylate, N,N-(2,2,4-trimethylhexamethylene)bis[2-(aminocarboxy)propane-1,3-diol] tetra(meth)acrylate, and 1,7-diacryloyloxy-2,2,6,6-tetra(meth)acryloyloxymethyl-4-oxyheptane. Among these, N,N-(2,2,4-trimethylhexamethylene)bis[2-(aminocarboxy)propane-1,3-diol] tetramethacrylate is preferred.

Among the above hydrophobic polymerizable monomers (B) having no acid group, difunctional aromatic polymerizable monomers and difunctional aliphatic polymerizable monomers are preferably used in terms of the mechanical strength and handling properties. Preferable examples of the difunctional aromatic polymerizable monomer are 2,2-bis[4-(3-(methacryloyloxy-2-hydroxypropoxy)phenyl]propane and 2,2-bis(4-methacryloyloxypolyethoxyphenyl)propane (having an average number of moles of added ethoxy groups of 2.6). Preferable examples of the Bifunctional aliphatic polymerizable monomers are glycerol di(meth)acrylate, triethylene glycol di(meth)acrylate, neopentyl glycol di(meth)acrylate, 1,6-hexanediol di(meth)acrylate, 1,10-decanediol di(meth)acrylate, 1,2-bis[3-methacryloxy-2-hydroxypropoxy]ethane, 2,2,4-trimethylhexamethylenebis(2-carbamoyloxyethyl) dimethacrylate, and N-methacryloyloxyethyl acrylamide.

Among the above hydrophobic polymerizable monomers (B) having no acid group, Bis-GMA, D-2.6E, 3G, UDMA, DD, and MAEA are more preferred and Bis-GMA, UDMA, and 3G are even more preferred in terms of the initial bond strength, the bond durability, and the mechanical strength to a tooth structure in wet condition. To exhibit high initial bond strength and high bond durability also to a tooth structure in dry condition and a high dentin cohesive failure rate also on a tooth structure in dry condition, Bis-GMA, D-2.6E, 3G, UDMA, DD, and MAEA are more preferred and D-2.6E, DD, and MAEA are even more preferred.

One of the hydrophobic polymerizable monomers (B) having no acid group may be contained alone, or a combination of two or more thereof may be contained. When the content of the hydrophobic polymerizable monomer (B) having no acid group is too high, the penetrability of the composition into tooth structures may decrease and thus its bond strength may decrease. When the content of the hydrophobic polymerizable monomer (B) having no acid group is too low, the improving effect on mechanical strength may not be obtained sufficiently. Thus, the content of the hydrophobic polymerizable monomer (B) having no acid group is preferably in the range of 9 to 90 parts by mass, more preferably in the range of 15 to 80 parts by mass, even more preferably in the range of 20 to 75 parts by mass, and most preferably in the range of 30 to 70 parts by mass, with respect to 100 parts by mass of the total polymerizable monomer components in the non-solvent dental adhesive composition. Meanwhile, to exhibit high initial bond strength and high bond durability also to a tooth structure in dry condition and a high dentin cohesive failure rate also on a tooth structure in dry condition, the content of the hydrophobic polymerizable monomer (B) having no acid group is preferably in the range of 40 to 99 parts by mass, more preferably in the range of 60 to 99 parts by mass, and most preferably in the range of 80 to 99 parts by mass, with respect to 100 parts by mass of the total polymerizable monomer components in the non-solvent dental adhesive composition.

[Hydrophilic Polymerizable Monomer (D) having no Acid Group]

As a hydrophilic polymerizable monomer (D) having no acid group, radical polymerizable monomers having no acid group and having a polymerizable group are preferred. The polymerizable group is preferably a (meth)acryl group and/or a (meth)acrylamide group in terms of ease of radical polymerization. The hydrophilic polymerizable monomer (D) having no acid group refers to a polymerizable monomer having no acid group and having a solubility of 10 mass % or more in water at 25° C. The hydrophilic polymerizable monomer (D) having no acid group preferably has a solubility of 30 mass % or more in water at 25° C. and is more preferably freely soluble in water at 25° C. The hydrophilic polymerizable monomer (D) having no acid group promotes the penetration of the other components of the non-solvent dental adhesive composition into a tooth structure. The hydrophilic polymerizable monomer (D) having no acid group itself also penetrates into a tooth structure and adheres to an organic component (collagen) in the tooth structure. As the hydrophilic polymerizable monomer (D) having no acid group, those having a hydrophilic group such as a hydroxyl group, an oxymethylene group, an oxyethylene group, an oxypropylene group, or an amide group are preferred. Examples of the hydrophilic polymerizable monomer (D) having no acid group include: hydrophilic monofunctional (meth)acrylate polymerizable monomers such as 2-hydroxyethyl (meth)acrylate, 3-hydroxypropyl (meth)acrylate, 2-hydroxypropyl (meth)acrylate, 1,3-dihydroxypropyl (meth)acrylate, 2,3-dihydroxypropyl (meth)acrylate, 2-trimethylammoniumethyl (meth)acrylchloride, and polyethylene glycol di(meth)acrylate (having 9 or more oxyethylene groups); and hydrophilic monofunctional (meth)acrylamide polymerizable monomers such as N-methylol (meth)acrylamide, N-hydroxyethyl (meth)acrylamide, N,N-(dihydroxyethyl) (meth)acrylamide, N-methoxymethyl (meth)acrylamide, N-ethoxymethyl (meth)acrylamide, diacetone (meth)acrylamide, 4-(meth)acryloylmorpholine, N-trihydroxymethyl-N-methyl (meth)acrylamide, and a monofunctional (meth)

acrylamide polymerizable monomer represented by the following general formula (3).

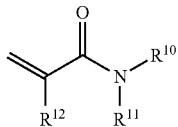

(3)

In the formula (3), $R^{10}$ and $R^{11}$ are each independently an optionally substituted, linear or branched alkyl group having 1 to 3 carbon atoms, and $R^{12}$ is a hydrogen atom or a methyl group.

The same substituent in the formula (1) can be used as $R^{10}$ or $R^{11}$. Examples of the alkyl group having 1 to 3 carbon atoms as $R^{10}$ or $R^{11}$ include a methyl group, an ethyl group, an n-propyl group, and an isopropyl group.

Among these hydrophilic polymerizable monomers (D) having no acid group, in terms of adhesion to tooth structures, 2-hydroxyethyl (meth)acrylate, 2,3-dihydroxypropyl (meth) acrylate, diacetone (meth) acrylamide, and hydrophilic monofunctional (meth)acrylamide polymerizable monomers are preferred, and 2-hydroxyethyl (meth)acrylate and a monofunctional (meth) acrylamide polymerizable monomer represented by the general formula (3) are more preferred. One of the hydrophilic polymerizable monomers (D) having no acid group may be contained alone, or a combination of two or more thereof may be contained.

Among the monofunctional (meth)acrylamide polymerizable monomers represented by the general formula (3), in terms of storage stability, N,N-dimethylacrylamide and N,N-diethylacrylamide are more preferred, and N,N-diethylacrylamide is most preferred.

In the present invention, when the content of the hydrophilic polymerizable monomer (D) having no acid group is too low, the improving effect on bond strength may not be obtained sufficiently. When the content of the hydrophilic polymerizable monomer (D) having no acid group is too high, the mechanical strength may decrease. Thus, the content of the hydrophilic polymerizable monomer (D) having no acid group is preferably in the range of 9 to 90 parts by mass, more preferably in the range of 15 to 80 parts by mass, even more preferably in the range of 20 to 75 parts by mass, and particularly preferably in the range of 30 to 70 parts by mass, with respect to 100 parts by mass of the total polymerizable monomer components in the non-solvent dental adhesive composition. Meanwhile, to exhibit high initial bond strength and high bond durability also to a tooth structure in dry condition and a high dentin cohesive failure rate also on a tooth structure in dry condition, the content of the hydrophilic polymerizable monomer (D) having no acid group is preferably in the range of 0 to 50 parts by mass, more preferably in the range of 0 to 20 parts by mass, and particularly preferably in the range of 0 to 10 parts by mass, with respect to 100 parts by mass of the total polymerizable monomer components in the non-solvent dental adhesive composition. The content of the hydrophilic polymerizable monomer (D) having no acid group may be 0.

In the non-solvent dental adhesive composition of the present invention, the content of the hydrophilic polymerizable monomer (D) having no acid group with respect to the total mass of the hydrophobic polymerizable monomer (B) having no acid group and the hydrophilic polymerizable monomer (D) having no acid group is preferably 50 mass % or less, more preferably 40 mass % or less, even more preferably 30 mass % or less, and particularly preferably 20 mass % or less in terms of exhibiting high initial bond strength and high bond durability also to a tooth structure in dry condition and a high dentin cohesive failure rate also on a tooth structure in dry condition. The content of the hydrophilic polymerizable monomer (D) having no acid group may be 0.

It is not known exactly why the non-solvent dental adhesive composition of the present invention exhibits high initial bond strength and high bond durability to dentin and a high dentin cohesive failure rate on dentin regardless of the condition (wet or dry condition) of the tooth surface when compositionally comprising a large amount of the hydrophobic polymerizable monomer (B) having no acid group. The reason for this is probably as follows. That is, the water-soluble photopolymerization initiator (C) is soluble in water and thus has poor solubility in the composition comprising a large amount of the hydrophobic polymerizable monomer (B) having no acid group. Consequently, when the non-solvent dental adhesive composition of the present invention has contact with a tooth structure (in wet or dry condition), the water-soluble photopolymerization initiator (C) moves to the tooth structure side where the water-soluble photopolymerization initiator (C) is more likely to dissolve and the non-solvent dental adhesive composition penetrates into the tooth structure and is cured. It is thought that the non-solvent dental adhesive composition of the present invention therefore has high initial bond strength and high bond durability also to a tooth structure in dry condition and a high dentin cohesive failure rate also on a tooth structure in dry condition.

[Water-Soluble Photopolymerization Initiator (C)]

The non-solvent dental adhesive composition of the present invention comprises the water-soluble photopolymerization initiator (C) having a solubility of 10 g/L or more in water at 25° C. The use of the water-soluble photopolymerization initiator (C) is the core of the technology of the present invention, and a combination of the water-soluble photopolymerization initiator (C) with the other components allows the non-solvent dental adhesive composition to achieve high initial bond strength, high bond durability, and a high dentin cohesive failure rate.

The solubility of the water-soluble photopolymerization initiator (C) in water at 25° C. is 10 g/L or more, preferably 15 g/L or more, even more preferably 20 g/L or more, and most preferably 25 g/L or more. If the solubility in water at 25° C. is less than 10 g/L, the water-soluble photopolymerization initiator (C) in the non-solvent dental adhesive composition of the present invention applied to a wet matter does not sufficiently dissolve in water of the wet matter at the adhesive interface portion. As a result, the polymerization promotion effect is less likely to be exhibited.

Examples of the water-soluble photopolymerization initiator (C) include: water-soluble acylphosphine oxides; water-soluble thioxanthones; α-hydroxyalkylacetophenones such as one resulting from introduction of a (poly)ethylene glycol chain into a hydroxy group of 1-[4-(2-hydroxyethoxy)-phenyl]-2-hydroxy-2-methyl-1-propan-1-one, one resulting from introduction of a (poly)ethylene glycol chain into a hydroxy group and/or a phenyl group of 1-hydroxycyclohexylphenylketone, one resulting from introduction of —OCH$_2$COO-Na+ into a phenyl group of 1-hydroxycyclohexylphenylketone, one resulting from introduction of a (poly)ethylene glycol chain into a hydroxy group and/or a phenyl group of 2-hydroxy-2-methyl-1-phenylpropane-1-one, and one resulting from introduction of —OCH$_2$COO-Nat into a phenyl group of 2-hydroxy-2-methyl-1-phenylpropane-1-one; and α-aminoalkylphenones, such as 2-methyl-1[4-(methylthio)phenyl]-2-morpholinopropane-1-one and 2-benzyl-2-dimethylamino-1-(4-morpholinophenyl)butanone-1, whose amino group is converted into a quaternary ammonium salt.

The water-soluble acylphosphine oxides are each represented by the following general formula (1) or (2).

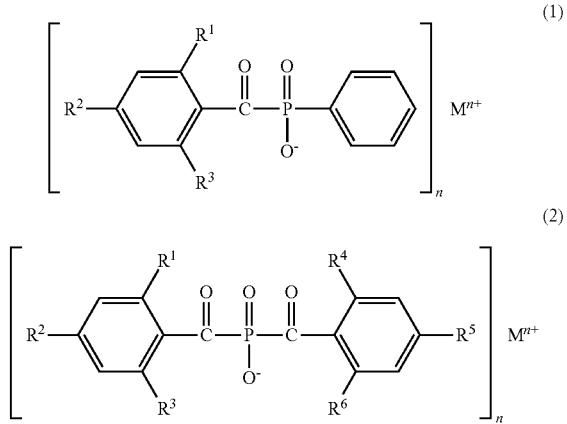

In the formulae, $R^1$, $R^2$, $R^3$, $R^4$, $R^5$, and $R^6$ are each independently a linear or branched alkyl group having 1 to 4 carbon atoms or a halogen atom; M is hydrogen ion, alkali metal ion, alkaline-earth metal ion, magnesium ion, pyridinium ion having an optionally substituted pyridine ring, or ammonium ion expressed by $HN^+R^7R^8R^9$, wherein $R^7$, $R^8$, and $R^9$ are each independently an organic group or a hydrogen atom; and n represents 1 or 2.

The alkyl group as $R^1$, $R^2$, $R^3$, $R^4$, $R^5$, or $R^6$ is not particularly limited as long as the alkyl group as $R^1$, $R^2$, $R^3$, $R^4$, $R^5$, or $R^6$ is a linear or branched alkyl group having 1 to 4 carbon atoms. Examples thereof include a methyl group, an ethyl group, an n-propyl group, an isopropyl group, an n-butyl group, an isobutyl group, a sec-butyl group, a 2-methylpropyl group, and a tert-butyl group. When M is a pyridinium ion, examples of the substituent in the pyridine ring include halogen atoms (fluorine, chlorine, bromine, and iodine atoms), a carboxy group, linear or branched acyl groups having 2 to 6 carbon atoms, linear or branched alkyl groups having 1 to 6 carbon atoms, and linear or branched alkoxy groups having 1 to 6 carbon atoms. M is preferably alkali metal ion, alkaline-earth metal ion, magnesium ion, pyridinium ion having an optionally substituted pyridine ring, or ammonium ion expressed by $HN^+R^7R^8R^9$, where the symbols are as defined above. Examples of the alkali metal ion include lithium ion, sodium ion, potassium ion, rubidium ion, and cesium ion. Examples of the alkaline-earth metal ion include calcium ion, strontium ion, barium ion, and radium ion. Examples of the organic group as $R^7$, $R^8$, or $R^9$ include those mentioned as examples of the substituent (exclusive of the halogen atoms) in the pyridine ring.

Among these, compounds in which $R^1$, $R^2$, $R^3$, $R^4$, $R^5$, and $R^6$ are each a methyl group are preferred in terms of the storage stability and color stability in the composition. Examples of the $M^{n+}$ include $Li^+$, $Na^+$, $K^+$, $Ca^{2+}$, $Mg^{2+}$, and ammonium ion derived from a variety of amines. Examples of the amines include ammonia, trimethylamine, diethylamine, dimethylaniline, ethylenediamine, triethanolamine, N,N-dimethylamino methacrylate, N,N-dimethylamino benzoic acid and alkyl esters thereof, N,N-diethylamino benzoic acid and alkyl esters thereof, and diethanol-para-toluidine.

Among these water-soluble acylphosphine oxides, sodium (2,4,6-trimethylbenzoyl)phenylphosphine oxide, lithium (2,4,6-trimethylbenzoyl)phenylphosphine oxide, sodium bis(2,4,6-trimethylbenzoyl)phosphine oxide, and lithium bis(2,4,6-trimethylbenzoyl)phosphine oxide are particularly preferred.

Water-soluble acylphosphine oxide compounds having such structures can be synthesized by a commonly-known method, and some of the water-soluble acylphosphine oxide compounds having such structures are commercially available. For example, the water-soluble acylphosphine oxide compounds having such structures can be synthesized by the methods disclosed in JP S57-197289, WO 2014/095724 A1, etc.

For example, 2-hydroxy-3-(9-oxo-9H-thioxanthene-4-yloxy)-N,N,N-trimethyl-1-propaneaminium chloride, 2-hydroxy-3-(1-methyl-9-oxo-9H-thioxanthene-4-yloxy)-N,N,N-trimethyl-1-propaneaminium chloride, 2-hydroxy-3-(9-oxo-9H-thioxanthene-2-yloxy)-N,N,N-trimethyl-1-propaneaminium chloride, 2-hydroxy-3-(3,4-dimethyl-9-oxo-9H-thioxanthene-2-yloxy)-N,N,N-trimethyl-1-propaneaminium chloride, 2-hydroxy-3-(3,4-dimethyl-9H-thioxanthene-2-yloxy)-N,N,N-trimethyl-1-propaneaminium chloride, or 2-hydroxy-3-(1,3,4-trimethyl-9-oxo-9H-thioxanthene-2-yloxy)-N,N,N-trimethyl-1-propaneaminium chloride can be used as the water-soluble thioxanthone.

The water-soluble photopolymerization initiator (C) may be dissolved in the non-solvent dental adhesive composition or may be dispersed in the composition in the form of powder as long as the water-soluble photopolymerization initiator (C) is soluble in water on the surface of a tooth structure (wet matter) and can selectively increase the polymerization curability of the adhesive interface portion and that of the inside of the resin-impregnated layer.

When the water-soluble photopolymerization initiator (C) is dissolved in the form of powder, the water-soluble photopolymerization initiator (C) having too large an average particle diameter tends to settle out. Therefore, the average particle diameter thereof is preferably 500 μm or less, more preferably 100 μm or less, and most preferably 50 μm or less. On the other hand, too small an average particle diameter excessively increases the specific surface area of the powder, resulting in a decrease of the amount of the water-soluble photopolymerization initiator (C) dispersible in the composition. Therefore, the average particle diameter thereof is preferably 0.01 μm or more. That is, the average particle diameter of the water-soluble photopolymerization initiator (C) is preferably in the range of 0.01 to 500 μm, more preferably in the range of 0.01 to 100 μm, and most preferably in the range of 0.01 to 50 μm.

The shape of the water-soluble photopolymerization initiator (C) dispersed in the form of powder is not particularly limited. Examples thereof include various shapes such as spherical, needle, sheet, and crushed shapes. The water-soluble photopolymerization initiator (C) can be produced by a conventionally known method, such as crushing, freeze-drying, or reprecipitation. The water-soluble photopolymerization initiator (C) can be obtained, for example, by any of the following methods.

Method 1: Method for obtaining the water-soluble photopolymerization initiator (C) by preparing an aqueous solution of the water-soluble photopolymerization initiator (C), freezing the aqueous solution at −50° C., and then vacuum-drying the frozen aqueous solution Method 2: Method for obtaining the water-soluble photopolymerization initiator (C) by preparing a saturated aqueous solution of the water-soluble photopolymerization initiator (C), pouring the aqueous solution into ethanol at 0° C., and filtering the resulting crystals, which are washed with ethanol and then air-dried Method 3: Method for obtaining the water-soluble photopolymerization initiator (C) by preparing a saturated aqueous solution of the water-soluble photopolymerization initiator (C), rapidly cooling the aqueous solution to 0° C., and then filtering and air-drying the resulting crystals Method 4: Method for obtaining the water-soluble photopolymerization initiator (C) by mechanical crushing and sieving The average particle diameter of the powder of the water-soluble photopolymerization initiator (C) can be calculated as the volume average particle diameter after image analysis of an electron microscope photograph of 100 or more particles with the use of an image analysis software (Mac-View manufactured by Mountech Co., Ltd.).

Among these methods for producing the water-soluble photopolymerization initiator (C), freeze-drying (method 1) and reprecipitation (method 2) are preferred and freeze-drying (method 1) is more preferred, in terms of the average particle diameter of the resulting powder.

The content of the water-soluble photopolymerization initiator (C) is preferably 0.01 to 20 parts by mass in terms of, for example, the curability of the resulting non-solvent dental adhesive composition, and is more preferably 0.05 to 10 parts by mass and even more preferably 0.1 to 5 parts by mass in terms of exhibiting high initial bond strength, high bond durability, and a high dentin cohesive failure rate, with respect to 100 parts by mass of the total polymerizable monomer components in the non-solvent dental adhesive composition. If the content of the water-soluble photopolymerization initiator (C) is less than 0.01 parts by mass, polymerization at the adhesive interface may not progress sufficiently and may cause a reduction in bond strength. The content of the water-soluble photopolymerization initiator (C) is more suitably 0.01 parts by mass or more. On the other hand, if the content of the water-soluble photopolymerization initiator (C) is more than 20 parts by mass and the polymerizability of the water-soluble photopolymerization initiator (C) is low, not only sufficient bond strength may not be obtained but also dissolution, dispersion, and diffusion thereof in the non-solvent dental adhesive composition may be insufficient.

[Water-Insoluble Photopolymerization Initiator (E)]

In addition to the water-soluble photopolymerization initiator (C), the non-solvent dental adhesive composition of the present invention may comprise a water-insoluble photopolymerization initiator (E) having a solubility of less than 10 g/L in water at 25° C. (hereinafter simply referred to as "water-insoluble photopolymerization initiator (E)") in terms of the curability. A commonly-known photopolymerization initiator can be used as the water-insoluble photopolymerization initiator (E) used in the present invention. One water-insoluble photopolymerization initiator (E) may be contained alone, or a combination of two or more thereof may be contained.

Examples of the water-insoluble photopolymerization initiator (E) include (bis)acylphosphine oxides different from the water-soluble photopolymerization initiator (C), thioxanthones, ketals, α-diketones, coumarins, anthraquinones, benzoin alkyl ether compounds, and α-aminoketone compounds.

Examples of the (bis)acylphosphine oxides include acylphosphine oxides such as 2,4,6-trimethylbenzoyldiphenylphosphine oxide, 2,6-dimethoxybenzoyldiphenylphosphine oxide, 2,6-dichlorobenzoyldiphenylphosphine oxide, 2,4,6-trimethylbenzoylmethoxyphenylphosphine oxide, 2,4,6-trimethylbenzoylethoxyphenylphosphine oxide, 2,3,5,6-tetramethylbenzoyldiphenylphosphine oxide, and benzoyl di-(2,6-dimethylphenyl)phosphonate. Other examples include bisacylphosphine oxides such as include bis(2,6-dichlorobenzoyl)phenylphosphine oxide, bis(2,6-dichlorobenzoyl)-2,5-dimethylphenylphosphine oxide, bis(2,6-dichlorobenzoyl)-4-propylphenylphosphine oxide, bis(2,6-dichlorobenzoyl)-1-naphthylphosphine oxide, bis(2,6-dimethoxybenzoyl)phenylphosphine oxide, bis(2,6-dimethoxybenzoyl-2,4,4-trimethylpentylphosphine oxide, bis(2,6-dimethoxybenzoyl)-2,5-dimethylphenylphosphine oxide, bis(2,4,6-trimethylbenzoyl)phenylphosphine oxide, and bis(2,5,6-trimethylbenzoyl)-2,4,4-trimethylpentylphosphine oxide.

Examples of the thioxanthones include thioxanthone and 2-chlorothioxanthene-9-one.

Examples of the ketals include benzyl dimethyl ketal and benzyl diethyl ketal.

Examples of the a-diketones include diacetyl, benzyl, camphorquinone, 2,3-pentadione, 2,3-octadione, 9,10-phenanthrenequinone, 4,4'-oxybenzyl, and acenaphthenequinone. Among these, camphorquinone is particularly preferred in that it shows maximum absorption at a wavelength in the visible region.

Examples of the coumarin compounds include compounds disclosed in JP H9-3109 A and JP H10-245525 A, such as 3,3'-carbonylbis(7-diethylaminocoumarin), 3-(4-methoxybenzoyl)coumarin, 3-thenoylcoumarin, 3-benzoyl-5,7-dimethoxycoumarin, 3-benzoyl-7-methoxycoumarin, 3-benzoyl-6-methoxycoumarin, 3-benzoyl-8-methoxycoumarin, 3-benzoylcoumarin, 7-methoxy-3-(p-nitrobenzoyl)coumarin, 3-(p-nitrobenzoyl)coumarin, 3,5-carbonylbis(7-methoxycoumarin), 3-benzoyl-6-bromocoumarin, 3,3'-carbonylbiscoumarin, 3-benzoyl-7-dimethylaminocoumarin, 3-benzoylbenzo[f]coumarin, 3-carboxycoumarin, 3-carboxy-7-methoxycoumarin, 3-ethoxycarbonyl-6-methoxycoumarin, 3-ethoxycarbonyl-8-methoxycoumarin, 3-acetylbenzo[f]coumarin, 3-benzoyl-6-nitrocoumarin, 3-benzoyl-7-diethylaminocoumarin, 7-dimethylamino-3-(4-methoxybenzoyl)coumarin, 7-diethylamino-3-(4-methoxybenzoyl)coumarin, 7-diethylamino-3-(4-diethylamino)coumarin, 7-methoxy-3-(4-methoxybenzoyl)coumarin, 3-(4-nitrobenzoyl)benzo[f]coumarin, 3-(4-ethoxycinnamoyl)-7-methoxycoumarin, 3-(4-dimethylaminocinnamoyl)coumarin, 3-(4-diphenylaminocinnamoyl)coumarin, 3-[(3-dimethylbenzothiazol-2-ylidene)acetyl]coumarin, 3-[(1-methylnaphto[1,2-d]thiazol-2-ylidene)acetyl]coumarin, 3,3'-carbonylbis(6-methoxycoumarin), 3,3'-carbonylbis(7-acetoxycoumarin), 3,3'-carbonylbis(7-dimethylaminocoumarin), 3-(2-benzothiazoyl)-7-(diethylamino)coumarin, 3-(2-benzothiazoyl)-7-(dibutylamino)coumarin, 3-(2-benzoimidazoyl)-7-(diethylamino)coumarin, 3-(2-benzothiazoyl)-7-(dioctylamino)coumarin, 3-acetyl-7-(dimethylamino)coumarin, 3,3'-carbonylbis(7-dibutylaminocoumarin), 3,3'-carbonyl-7-diethylaminocoumarin-7'-bisbiitoxyethyl) aminocoumarin, 10-[3-[4-(dimethylamino)phenyl]-1-oxo-2-prop enyl]-2,3,6,7-tetrahydro-1,1,7,7-tetram ethyl-1H,5H, 11H-[1]benzopyrano[6,7,8-ij]quinolizin-11-one, and 10-(2-benzothiazoyl)-2,3,6,7-tetrahydro-1,1,7,7-tetramethyl-1H,5H, 11H-[1]benzopyrano[6,7,8-ij]quinolizin-11-one.

Among the above coumarin compounds, 3,3'-carbonylbis(7-diethylaminocoumarin) and 3,3'-carbonylbis(7-dibutylaminocoumarin) are particularly suitable.

Examples of the anthraquinones include anthraquinone, 1-chloroanthraquinone, 2-chloroanthraquinone, 1-bromoanthraquinone, 1,2-benzanthraquinone, 1-methylanthraquinone, 2-ethylanthraquinone, and 1-hydroxyanthraquinone.

Examples of the benzoin alkyl ether compounds include benzoin methyl ether, benzoin ethyl ether, benzoin isopropyl ether, and benzoin isobutyl ether.

Examples of the α-aminoketone compounds include 2-methyl-1-[4-(methylthio)phenyl]-2-morpholinopropan-1-one.

Among these water-insoluble photopolymerization initiators (E), at least one selected from the group consisting of the (bis)acylphosphine oxides, the α-diketones, and the coumarin compounds is preferably used. The use thereof contributes to obtaining the non-solvent dental adhesive composition excellent in photocurability under visible or near-ultraviolet light irradiation and exhibiting sufficient photocurability by light irradiation using any light source selected from a halogen lamp, a light-emitting diode (LED), and a xenon lamp.

The content of the water-insoluble photopolymerization initiator (E) is not particularly limited. In terms of, for example, the curability of the resulting composition, the content of the water-insoluble photopolymerization initiator (E) is preferably in the range of 0.01 to 10 mass %, more preferably in the range of 0.05 to 7 mass %, and most preferably in the range of 0.1 to 5 mass %, with respect to 100 parts by mass of the total polymerizable monomer components in the non-solvent dental adhesive composition. If the content of the water-insoluble photopolymerization initiator (E) is more than 10 mass % and the polymerizability of the photopolymerization initiator itself is low, not only sufficient bond strength may not be obtained but also precipitation from the non-solvent dental adhesive composition may occur.

The mass ratio [(C):(E)] between the water-soluble photopolymerization initiator (C) and the water-insoluble photopolymerization initiator (E) in the present invention is preferably 10:1 to 1:10, more preferably 7:1 to 1:7, even more preferably 5:1 to 1:5, and most preferably 3:1 to 1:3. If the water-soluble photopolymerization initiator (C) is contained in such a large amount that the mass ratio is beyond 10:1, the curability of the non-solvent dental adhesive composition itself may decrease and it may become difficult to exhibit high initial bond strength, high bond durability, and a high dentin cohesive failure rate. If the water-insoluble photopolymerization initiator (E) is contained in such a large amount that the mass ratio is beyond 1:10, the curability of the non-solvent dental adhesive composition itself may be increased. However, in that case, the polymerization at the adhesive interface portion is not promoted sufficiently and it may become difficult to exhibit high initial bond strength, high bond durability, and a high dentin cohesive failure rate.

[Chemical Polymerization Initiator]

The non-solvent dental adhesive composition of the present invention can further comprise a chemical polymerization initiator, and organic peroxides are preferably used as the chemical polymerization initiator. The organic peroxides that may be used as the chemical polymerization initiator are not particularly limited, and commonly-known organic peroxides can be used. Typical examples of the organic peroxides include ketone peroxides, hydroperoxides, diacyl peroxides, dialkyl peroxides, peroxyketals, peroxyesters, and peroxydicarbonates. Specific examples of these organic peroxides include those disclosed in WO 2008/087977 A1.

[Polymerization Accelerator (F)]

In another embodiment, a polymerization accelerator (F) is used together with the water-insoluble photopolymerization initiator (E) and/or the chemical polymerization initiator. Examples of the polymerization accelerator (F) used in the present invention include amines, sulfinic acids and salts thereof, borate compounds, barbituric acid derivatives, triazine compounds, copper compounds, tin compounds, vanadium compounds, halogen compounds, aldehydes, thiol compounds, sulfites, hydrogen sulfites, and thiourea compounds.

The amines used as the polymerization accelerator (F) are classified into aliphatic amines and aromatic amines. Examples of the aliphatic amines include: primary aliphatic amines such as n-butylamine, n-hexylamine, and n-octylamine; secondary aliphatic amines such as diisopropylamine, dibutylamine, and N-methylethanolamine; and tertiary aliphatic amines such as N-methyldiethanolamine, N-ethyldiethanolamine, N-n-butyldiethanolamine, N-lauryldiethanolamine, 2-(dimethylamino)ethyl methacrylate, N-methyldiethanolamine dimethacrylate, N-ethyldiethanolamine dimethacrylate, triethanolamine monomethacrylate, triethanolamine dimethacrylate, triethanolamine trimethacrylate, triethanolamine, trimethylamine, triethylamine, and tributylamine. Among these, the tertiary aliphatic amines are preferred in terms of the curability and storage stability of the non-solvent dental adhesive composition and, in particular, N-methyldiethanolamine and triethanolamine are more preferably used.

Examples of the aromatic amines include N,N-bis(2-hydroxyethyl)-3,5-dimethylaniline, N,N-bis(2-hydroxyethyl)-p-toluidine, N,N-bis(2-hydroxyethyl)-3,4-dimethylaniline, N,N-bis(2-hydroxyethyl)-4-ethylaniline, N,N-bis(2-hydroxyethyl)-4-isopropylaniline, N,N-bis(2-hydroxyethyl)-4-t-butylaniline, N,N-bis(2-hydroxyethyl)-3,5-di-isopropylaniline, N,N-bis(2-hydroxyethyl)-3,5-di-t-butylaniline, N,N-dimethylaniline, N,N-dimethyl-p-toluidine, N,N-dimethyl-m-toluidine, N,N-diethyl-p-toluidine, N,N-dimethyl-3,5-dimethylaniline, N,N-dimethyl-3,4-dimethylaniline, N,N-dimethyl-4-ethylaniline, N,N-dimethyl-4-isopropylaniline, N,N-dimethyl-4-t-butylaniline, N,N-dimethyl-3,5-di-t-butylaniline, ethyl 4-(N,N-dimethylamino)benzoate, methyl 4-(N,N-dimethylamino)benzoate, propyl 4-(N,N-dimethylamino)benzoate, n-butoxyethyl 4-(N,N-dimethylamino)benzoate, 2-(methacryloyloxy)ethyl 4-(N,N-dimethylamino)benzoate, 4-(N,N-dimethylamino)benzophenone, and butyl 4-(N,N-dimethylamino)benzoate. Among these, at least one selected from the group consisting of N,N-bis(2-hydroxyethyl)-p-toluidine, ethyl 4-(N,N-dimethylamino)benzoate, n-butoxyethyl 4-(N,N-dimethylamino)benzoate, and 4-(N,N-dimethylamino)benzophenone is preferably used in terms of the ability to impart excellent curability to the non-solvent dental adhesive composition.

Specific examples of the sulfinic acids and salts thereof, borate compounds, barbituric acid derivatives, triazine compounds, copper compounds, tin compounds, vanadium compounds, halogen compounds, aldehydes, thiol compounds, sulfites, hydrogen sulfites, and thiourea compounds include those disclosed in WO 2008/087977 A1.

One of the polymerization accelerators (F) may be contained alone, or a combination of two or more thereof may be contained. The content of the polymerization accelerator (F) used in the present invention is not particularly limited. In terms of, for example, the curability of the resulting non-solvent dental adhesive composition, the content of the polymerization accelerator (F) is preferably 0.001 to 30 parts by mass, more preferably 0.01 to 10 parts by mass, and most preferably 0.1 to 5 parts by mass, with respect to 100 parts by mass of the total polymerizable monomer components in the non-solvent dental adhesive composition. If the content of the polymerization accelerator (F) is less than 0.001 parts by mass, polymerization may not progress sufficiently and may cause a reduction in adhesiveness. The content of the polymerization accelerator (F) is more suitably 0.05 parts by mass or more. If the content of the polymerization accelerator (F) is more than 30 parts by mass and the polymerizability of the polymerization initiator itself is low, not only sufficient adhesiveness may not be obtained but also precipitation from the non-solvent dental adhesive composition may occur. Therefore, the content of the polymerization accelerator (F) is more suitably 20 parts by mass or less.

[Filler (G)]

Depending on the embodiment employed, the non-solvent dental adhesive composition of the present invention may further comprise a filler (G). The filler (G) is typically classified broadly into an organic filler, an inorganic filler, and an organic-inorganic composite filler. Examples of the material of the organic filler include polymethyl methacrylate, polyethyl methacrylate, methyl methacrylate-ethyl methacrylate copolymer, cross-linked polymethyl methacrylate, cross-linked polyethyl methacrylate, polyamide, polyvinyl chloride, polystyrene, chloroprene rubber, nitrile rubber, ethylene-vinyl acetate copolymer, styrene-butadiene copolymer, acrylonitrile-styrene copolymer, and acrylonitrile-styrene-butadiene copolymer. One of these may be used alone or a mixture of two or more thereof can be used. The shape of the organic filler is not particularly limited, and the particle diameter of the filler used can be selected as appropriate. In terms of the characteristics such as handling properties and mechanical strength of the resulting non-solvent dental adhesive composition, the average particle diameter of the organic filler is preferably 0.001 to 50 µm and more preferably 0.001 to 10 µm.

Examples of the material of the inorganic filler include quartz, silica, alumina, silica-titania, silica-titania-barium oxide, silica-zirconia, silica-alumina, lanthanum glass, borosilicate glass, soda glass, barium glass, strontium glass, glass ceramic, aluminosilicate glass, barium boroaluminosilicate glass, strontium boroaluminosilicate glass, fluoroaluminosilicate glass, calcium fluoroaluminosilicate glass, strontium fluoroaluminosilicate glass, barium fluoroaluminosilicate glass, and strontium calcium fluoroaluminosilicate glass. These may also be used alone or as a mixture of two or more thereof. The shape of the inorganic filler is not particularly limited, and the particle diameter of the filler used can be selected as appropriate. In terms of the characteristics such as handling properties and mechanical strength of the resulting composition, the average particle diameter of the inorganic filler is preferably 0.001 to 50 µm and more preferably 0.001 to 10 µm.

Examples of the shape of the inorganic filler include an irregular shape and a spherical shape. The inorganic filler used is preferably a spherical filler in terms of enhancement of the mechanical strength of the composition. Furthermore, the use of a spherical filler is also advantageous in that when the non-solvent dental adhesive composition of the present invention is used as a self-adhesive dental composite resin, a composite resin having excellent surface gloss can be obtained. The term "spherical filler" as used herein refers to a filler whose particles are rounded in shape as observed in a unit area of field of view in a photograph of the filler taken by an electron microscope and have an average aspect ratio of 0.6 or more calculated as an average of values determined by dividing a diameter of each particle in a direction perpendicular to the maximum diameter of the particle by the maximum diameter. The average particle diameter of the spherical filler is preferably 0.05 to 5 µm. An average particle diameter of less than 0.05 µm could cause a lower degree of filling of the compound with the spherical filler and hence reduced mechanical strength. An average particle diameter of more than 5 µm could cause a reduction in the surface area of the spherical filler, resulting in a failure to obtain a cured product formed of the non-solvent dental adhesive composition and having high mechanical strength.

The inorganic filler may be surface-treated beforehand with a commonly-known surface treatment agent such as a silane coupling agent where necessary in order to adjust the flowability of the non-solvent dental adhesive composition. Examples of the surface treatment agent include vinyltrimethoxysilane, vinyltriethoxysilane, vinyltrichlorosilane, vinyltri(β-methoxyethoxy)silane, γ-methacryloyloxypropyltrimethoxysilane, 8-methacryloyloxyoctyltrimethoxysilane, 11-methacryloyloxyundecyltrimethoxysilane, γ-glycidoxypropyltrimethoxysilane, γ-mercaptopropyltrimethoxysilane, and γ-aminopropyltriethoxysilane.

The organic-inorganic composite filler used in the present invention is obtainable by adding a polymerizable monomer compound to the above inorganic filler, forming the mixture into a paste, then subjecting the paste to polymerization, and crushing the resulting polymer product. The organic-inorganic composite filler used can be, for example, a TMPT filler (obtainable by mixing trimethylolpropane methacrylate and a silica filler, subjecting the mixture to polymerization, and then crushing the resulting polymer product). The shape of the organic-inorganic composite filler is not particularly limited, and the particle diameter of the filler used can be selected as appropriate. In terms of the characteristics such as handling properties and mechanical strength of the resulting composition, the average particle diameter of the organic-inorganic composite filler is preferably 0.001 to 50 µm and more preferably 0.001 to 10 µm.

In the present specification, the average particle diameter of the filler (h) can be determined by laser diffraction scattering method or by electron microscope observation of the particles. Specifically, the laser diffraction scattering method is convenient for particle diameter measurement on particles with a diameter of 0.1 lam or more, and electron microscope observation is convenient for particle diameter measurement on ultrafine particles with a diameter of less than 0.1 µm. The particle diameter of 0.1 µm is a value determined by the laser diffraction scattering method.

To be specific about the laser diffraction scattering method, for example, the average particle diameter can be measured using a 0.2% aqueous solution of sodium hexametaphosphate as a dispersion medium by means of a laser diffraction particle size distribution analyzer (SALD-2100 manufactured by Shimadzu Corporation).

To be more specific about the electron microscope observation, for example, the average particle diameter can be determined by taking a photograph of particles by means of an electron microscope (S-4000 manufactured by Hitachi, Ltd.) and measuring the particle diameters of (200 or more) particles observed in a unit area of field of view in the photograph by the use of an image-analyzing particle size distribution analysis software (Mac-View (Mountech Co., Ltd.)). In this case, the particle diameter of each particle is determined as an arithmetic mean of the maximum and minimum lengths of the particle, and, from the thus determined particle diameters and the number of the particles, the average primary particle diameter is calculated.

In the present invention, two or more types of fillers differing in material, particle size distribution, and form, may be mixed or used in combination. Additionally, particles other than the filler may be accidentally contained as impurities to the extent that the other particles do not impair the effect of the present invention.

The content of the filler (G) used in the present invention is not particularly limited. The content of the filler (G) is preferably 0 to 2000 parts by mass with respect to 100 parts by mass of the total polymerizable monomer components in the non-solvent dental adhesive composition. The suitable content of the filler (G) greatly differs depending on the embodiment employed. Therefore, along with the later-described descriptions of specific embodiments of the non-solvent dental adhesive composition of the present invention, the suitable content of the filler (G) for each embodiment will be shown.

[Fluorine Ion-Releasing Material]

The non-solvent dental adhesive composition of the present invention may further comprise a fluorine ion-releasing material. The non-solvent dental adhesive composition in which the fluorine ion-releasing material is contained can impart acid resistance to tooth structures. Examples of the fluorine ion-releasing material include metal fluorides such as sodium fluoride, potassium fluoride, sodium monofluorophosphate, lithium fluoride, and ytterbium fluoride. One of these fluorine ion-releasing materials may be contained alone, or a combination of two or more thereof may be contained.

Furthermore, for example, a pH adjuster, a polymerization inhibitor, a thickener, a colorant, a fluorescent agent, or a flavor may be contained in the non-solvent dental adhesive composition to the extent that the effect of the present invention is not impaired. Additionally, an antibacterial substance such as cetylpyridinium chloride, benzalkonium chloride, (meth)acryloyloxydodecylpyridinium bromide, (meth)acryloyloxyhexadecylpyridinium chloride, (meth)acryloyloxydecylammonium chloride, or triclosan may be contained in the non-solvent dental adhesive composition.

A commonly-known dye or pigment may be contained in the non-solvent dental adhesive composition of the present invention.

The non-solvent dental adhesive composition of the present invention can be used, for example, for a dental bonding material, a self-adhesive dental composite resin, a dental cement, a pit and fissure sealant, a mobile tooth fixing material, and an orthodontic adhesive. The non-solvent dental adhesive composition of the present invention can be suitably used particularly as a dental bonding material, a self-adhesive dental composite resin, and a dental cement. When used as such, the non-solvent dental adhesive composition of the present invention may be a two-part composition in which the components thereof are divided into two. Specific embodiments in which the non-solvent dental adhesive composition is employed will be described hereinafter.

<Dental Bonding Material>

The use of the non-solvent dental adhesive composition as a dental bonding material is one of the suitable embodiments of the present invention. The dental bonding material is a bonding material allowing a demineralization step, a penetration step, and a curing step to be performed in one step and being substantially free of water and an organic solvent. Examples of the dental bonding material include a two-part material used by mixing two separated parts which are a liquid A and a liquid B immediately before use and a one-part material which can be directly used. In particular, the use of a one-part material is advantageous because of much simplified steps. The non-solvent dental adhesive composition used for the dental bonding material is preferably a composition comprising the acid group-containing polymerizable monomer (A), the hydrophobic polymerizable monomer (B) having no acid group, the hydrophilic polymerizable monomer (D) having no acid group, the water-soluble photopolymerization initiator (C), the water-insoluble photopolymerization initiator (E), the polymerization accelerator (F), and the filler (G).

The dental bonding material preferably contains 1 to 90 parts by mass of the acid group-containing polymerizable monomer (A), 1 to 90 parts by mass of the hydrophobic polymerizable monomer (B) having no acid group, and 0 to 90 parts by mass of the hydrophilic polymerizable monomer (D) having no acid group, and more preferably contains 5 to 80 parts by mass of the acid group-containing polymerizable monomer (A), 5 to 80 parts by mass of the hydrophobic polymerizable monomer (B) having no acid group, and 1 to 80 parts by mass of the hydrophilic polymerizable monomer (D) having no acid group, with respect to 100 parts by mass of the total polymerizable monomer components in the non-solvent dental adhesive composition. Additionally, the dental bonding material preferably contains 0.001 to 30 parts by mass of the water-soluble photopolymerization initiator (C), 0.001 to 30 parts by mass of the water-insoluble photopolymerization initiator (E), 0.001 to 20 parts by mass of the polymerization accelerator (F), and 0 to 100 parts by mass of the filler (G), and more preferably contains 0.05 to 10 parts by mass of the water-soluble photopolymerization initiator (C), 0.05 to 10 parts by mass of the water-insoluble photopolymerization initiator (E), 0.05 to 10 parts by mass of the polymerization accelerator (F), and 1 to 50 parts by mass of the filler (G), with respect to 100 parts by mass of the total polymerizable monomer components. Meanwhile, to exhibit high initial bond strength and high bond durability also to a tooth structure in dry condition and a high dentin cohesive failure rate also on a tooth structure in dry condition, the dental bonding material preferably contains 1 to 90 parts by mass of the acid group-containing polymerizable monomer (A), 1 to 99 parts by mass of the hydrophobic polymerizable monomer (B) having no acid group, and 0 to 90 parts by mass of the hydrophilic polymerizable monomer (D) having no acid group, more preferably contains 1 to 80 parts by mass of the acid group-containing polymerizable monomer (A), 10 to 99 parts by mass of the hydrophobic polymerizable monomer (B) having no acid group, and 0 to 80 parts by mass of the hydrophilic polymerizable monomer (D) having no acid group, and even more preferably contains 1 to 80 parts by mass of the acid group-containing polymerizable monomer (A), 10 to 99 parts by mass of the hydrophobic polymerizable monomer (B) having no acid group, and 0 to 50 parts by mass of the hydrophilic polymerizable monomer (D) having no acid group, with respect to 100 parts by mass of the total polymerizable monomer components in the non-solvent dental adhesive composition. Additionally, the dental bonding material preferably contains 0.001 to 30 parts by mass of the water-soluble photopolymerization initiator (C), 0.001 to 30 parts by mass of the water-insoluble photopolymerization initiator (E), 0.001 to 20 parts by mass of the polymerization accelerator (F), and 0 to 100 parts by mass of the filler (G), and more preferably contains 0.05 to 10 parts by mass of the water-soluble photopolymerization initiator (C), 0.05 to 10 parts by mass of the water-insoluble photopolymerization initiator (E), 0.05 to 10 parts by mass of the polymerization accelerator (F), and 1 to 50 parts by mass of the filler (G), with respect to 100 parts by mass of the total polymerizable monomer components.

<Self-Adhesive Dental Composite Resin>

The use of the non-solvent dental adhesive composition as a self-adhesive dental composite resin is another suitable embodiment of the present invention. In particular, composite resins that are filling composite resins having the adhesiveness have been under development in recent years. The use of such composite resins is advantageous because of steps much more simplified than those of the adhesion system of the above dental bonding material. The non-solvent dental adhesive composition used as a self-adhesive dental composite resin preferably comprises the acid group-containing polymerizable monomer (A), the hydrophobic polymerizable monomer (B) having no acid group, the hydrophilic polymerizable monomer (D) having no acid group, the water-soluble photopolymerization initiator (C), the water-insoluble photopolymerization initiator (E), the polymerization accelerator (F), and the filler (G).

The self-adhesive dental composite resin preferably contains 1 to 90 parts by mass of the acid group-containing polymerizable monomer (A), 1 to 90 parts by mass of the hydrophobic polymerizable monomer (B) having no acid group, and 0 to 90 parts by mass of the hydrophilic polymerizable monomer (D) having no acid group, and more preferably contains 5 to 80 parts by mass of the acid group-containing polymerizable monomer (A), 5 to 80 parts by mass of the hydrophobic polymerizable monomer (B) having no acid group, and 1 to 80 parts by mass of the hydrophilic polymerizable monomer (D) having no acid group, with respect to 100 parts by mass of the total polymerizable monomer components in the non-solvent dental adhesive composition. Additionally, the self-adhesive dental composite resin preferably contains 0.001 to 30 parts by mass of the water-soluble photopolymerization initiator (C), 0.001 to 30 parts by mass of the water-insoluble photopolymerization initiator (E), 0.001 to 20 parts by mass of the polymerization accelerator (F), and 50 to 2000 parts by mass of the filler (G), and more preferably contains 0.05 to 10 parts by mass of the water-soluble photopolymerization initiator (C), 0.05 to 10 parts by mass of the water-insoluble photopolymerization initiator (E), 0.05 to 10 parts by mass of the polymerization accelerator (F), and 100 to 1500 parts by mass of the filler (G), with respect to 100 parts by mass of the total polymerizable monomer components. Meanwhile, to exhibit high initial bond strength and high bond durability also to a tooth structure in dry condition and a high dentin cohesive failure rate also on a tooth structure in dry condition, the self-adhesive dental composite resin preferably contains 1 to 90 parts by mass of the acid group-containing polymerizable monomer (A), 1 to 99 parts by mass of the hydrophobic polymerizable monomer (B) having no acid group, and 0 to 90 parts by mass of the hydrophilic polymerizable monomer (D) having no acid group, more preferably contains 1 to 80 parts by mass of the acid group-containing polymerizable monomer (A), 10 to 99 parts by mass of the hydrophobic polymerizable monomer (B) having no acid group, and 0 to 80 parts by mass of the hydrophilic polymerizable monomer (D) having no acid group, and even more preferably contains 1 to 80 parts by mass of the acid group-containing polymerizable monomer (A), 10 to 99 parts by mass of the hydrophobic polymerizable monomer (B) having no acid group, and 0 to 50 parts by mass of the hydrophilic polymerizable monomer (D) having no acid group, with respect to 100 parts by mass of the total polymerizable monomer components in the non-solvent dental adhesive composition. Additionally, the self-adhesive dental composite resin preferably contains 0.001 to 30 parts by mass of the water-soluble photopolymerization initiator (C), 0.001 to 30 parts by mass of the water-insoluble photopolymerization initiator (E), 0.001 to 20 parts by mass of the polymerization accelerator (F), and 50 to 2000 parts by mass of the filler (G), and more preferably contains 0.05 to 10 parts by mass of the water-soluble photopolymerization initiator (C), 0.05 to 10 parts by mass of the water-insoluble photopolymerization initiator (E), 0.05 to 10 parts by mass of the polymerization accelerator (F), and 100 to 1500 parts by mass of the filler (G), with respect to 100 parts by mass of the total polymerizable monomer components.

<Dental Cement>

The use of the non-solvent dental adhesive composition as a dental cement is another suitable embodiment of the present invention. Suitable examples of the dental cement include a resin cement, a glass ionomer cement, and a resin-reinforced glass ionomer cement. A self-etching primer, for example, may be used as a pretreatment material for the dental cement.

The dental cement preferably contains 1 to 90 parts by mass of the acid group-containing polymerizable monomer (A), 1 to 90 parts by mass of the hydrophobic polymerizable monomer (B) having no acid group, and 0 to 90 parts by mass of the hydrophilic polymerizable monomer (D) having no acid group, and more preferably contains 5 to 80 parts by mass of the acid group-containing polymerizable monomer (A), 5 to 80 parts by mass of the hydrophobic polymerizable monomer (B) having no acid group, and 1 to 80 parts by mass of the hydrophilic polymerizable monomer (D) having no acid group, with respect to 100 parts by mass of the total polymerizable monomer components in the non-solvent dental adhesive composition. Additionally, the dental cement preferably contains 0.001 to 30 parts by mass of the water-soluble photopolymerization initiator (C), 0.001 to 30 parts by mass of the water-insoluble photopolymerization initiator (E), 0.001 to 20 parts by mass of the polymerization accelerator (F), and 50 to 2000 parts by mass of the filler (G), and more preferably contains 0.05 to 10 parts by mass of the water-soluble photopolymerization initiator (C), 0.05 to 10 parts by mass of the water-insoluble photopolymerization initiator (E), 0.05 to 10 parts by mass of the polymerization accelerator (F), and 100 to 1500 parts by mass of the filler (G), with respect to 100 parts by mass of the total polymerizable monomer components. Meanwhile, to exhibit high initial bond strength and high bond durability also to a tooth structure in dry condition and a high dentin cohesive failure rate also on a tooth structure in dry condition, the dental cement preferably contains 1 to 90 parts by mass of the acid group-containing polymerizable monomer (A), 1 to 99 parts by mass of the hydrophobic polymerizable monomer (B) having no acid group, and 0 to 90 parts by mass of the hydrophilic polymerizable monomer (D) having no acid group, more preferably contains 1 to 80 parts by mass of the acid group-containing polymerizable monomer (A), 10 to 99 parts by mass of the hydrophobic polymerizable monomer (B) having no acid group, and 0 to 80 parts by mass of the hydrophilic polymerizable monomer (D) having no acid group, and even more preferably contains 1 to 80 parts by mass of the acid group-containing polymerizable monomer (A), 10 to 99 parts by mass of the hydrophobic polymerizable monomer (B) having no acid group, and 0 to 50 parts by mass of the hydrophilic polymerizable monomer (D) having no acid group, with respect to 100 parts by mass of the total polymerizable monomer components in the non-solvent dental adhesive composition. Additionally, the dental cement preferably contains 0.001 to 30 parts by mass of the water-soluble photopolymerization initiator (C), 0.001 to 30 parts by mass of the water-insoluble photopolymerization initiator (E), 0.001 to 20 parts by mass of the polymerization accelerator (F), and 50 to 2000 parts by mass of the filler (G), and more preferably contains 0.05 to 10 parts by mass of the water-soluble photopolymerization initiator (C), 0.05 to 10 parts by mass of the water-insoluble photopolymerization initiator (E), 0.05 to 10 parts by mass of the polymerization accelerator (F), and 100 to 1500 parts by mass of the filler (G), with respect to 100 parts by mass of the total polymerizable monomer components.

For any of the above suitable embodiments, namely, the dental bonding material, the self-adhesive dental composite resin, and the dental cement, adjustment of the contents of the components, and addition or omission of some of the components can be done on the basis of the foregoing description in the present specification.

As described above, in the non-solvent dental adhesive composition of the present invention may be incorporated a small amount (for example, 3 mass % or less with respect to the composition) of moisture or an organic solvent as long as no trouble such as insufficient curing or delay in curing is caused. The content of water and an organic solvent is preferably 1 mass % or less and more preferably 0.1 mass % or less with respect to the composition.

The present invention encompasses embodiments obtainable by combining the above embodiments in various manners within the technical scope of the present invention as long as the effect of the present invention can be obtained.

EXAMPLES

The present invention will now be described in more detail by way of Examples. It should be noted that the present invention is not limited to Examples given below. Not all combinations of features described in Examples are necessarily essential for the solution to the problem of the present invention. Components used in the following Examples and Comparative Examples, their abbreviations and structures, and testing methods are as follows.

[Acid Group-Containing Polymerizable Monomer (A)]

MDP: 10-methacryloyloxydecyl dihydrogen phosphate

[Hydrophobic Polymerizable Monomer (B) having no Acid Group]

Bis-GMA: 2,2-bis[4-(3-methacryloyloxy-2-hydroxypropoxy)phenyl]propane

UDMA: 2,2,4-trimethylhexamethylenebis(2-carbamoyloxyethyl) dimethacrylate

3G: triethylene glycol dimethacrylate

DD: 1,10-decanediol dimethacrylate

MAEA: N-methacryloyloxyethyl acrylamide

[Hydrophilic Polymerizable Monomer (D) having no Acid Group]

HEMA: 2-hydroxyethyl methacrylate

DEAA: N,N-diethylacrylamide

[Water-Soluble Photopolymerization Initiator (C)]

Li-TPO: lithium (2,4,6-trimethylbenzoyl)phenylphosphine oxide (compound represented by the following formula (4))

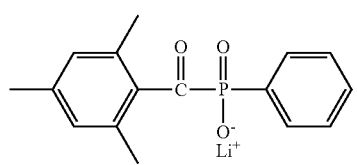

Solubility in water at 25° C.: 45 g/L

Na-TPO: sodium (2,4,6-trimethylbenzoyl)phenylphosphine oxide (compound represented by the following formula (5))

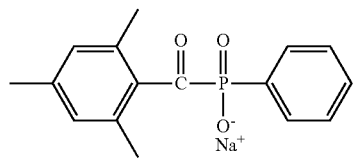

Solubility in water at 25° C.: 28 g/L

BAPO-OLi: lithium bis(2,4,6-trimethylbenzoyl)phosphine oxide (compound represented by the following formula (6))

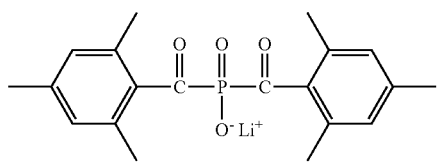

Solubility in water at 25° C.: 52 g/L

BAPO-ONa: sodium bis(2,4,6-trimethylbenzoyl)phosphine oxide (compound represented by the following formula (7))

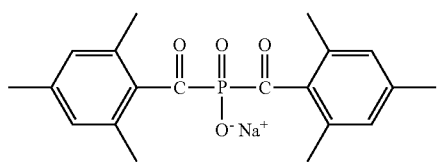

Solubility in water at 25° C.: 60 g/L

[Water-Insoluble Photopolymerization Initiator (E)]

TMDPO-A1 (compound represented by the following formula (8))

(8)

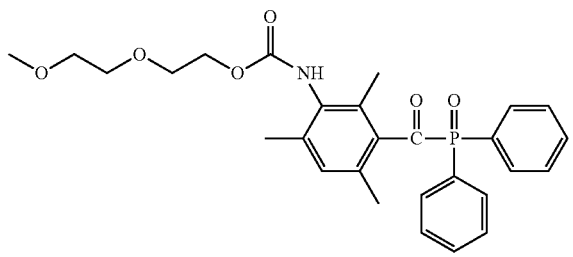

Solubility in water at 25° C.<10 g/L
BAPO-A1 (compound represented by the following formula (9))

(9)

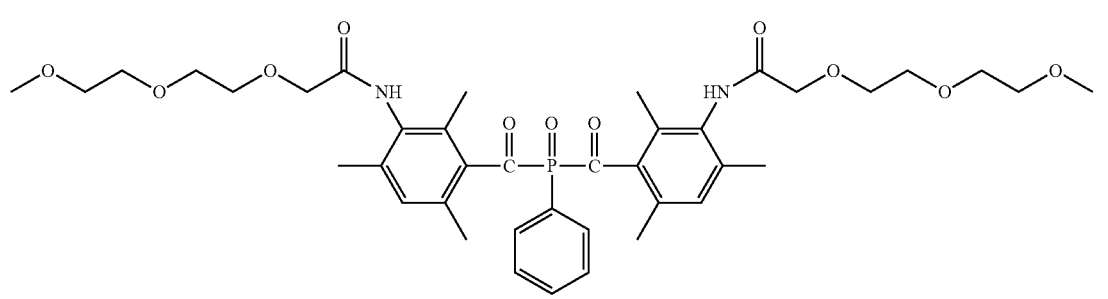

Solubility in water at 25° C.<10 g/L
CQ: dl-camphorquinone
Solubility in water at 25° C.: 1.7 g/L
TMDPO: 2,4,6-trimethylbenzoykliphenylphosphine oxide
Solubility in water at 25° C.:<1 g/L
BAPO: bis(2,4,6-trimethylbenzoyl)phenylphosphine oxide
Solubility in water at 25° C.:<1 g/L
[Polymerization Accelerator (F)]
DABE: ethyl 4-(N,N-dimethylamino)benzoate
[Filler (G)]
Inorganic filler 1: Fine particle silica "Aerosil R 972" manufactured by Nippon Aerosil Co., Ltd., average particle diameter: 16 nm
Inorganic filler 2: Fine particle silica "Aerosil 380" manufactured by Nippon Aerosil Co., Ltd., average particle diameter: 7 nm
Inorganic filler 3: Silane-treated silica powder
Silica powder (manufactured by Nitchitsu Co., Ltd. under the trade name Hi-Silica) was ground in a ball mill to obtain a pulverized silica powder. The average particle diameter of the pulverized silica powder thus obtained was measured using a laser diffraction particle size distribution analyzer (manufactured by Shimadzu Corporation, Model "SALD-2100"). The average particle diameter was 2.2 µm. 100 parts by mass of this pulverized silica powder was surface-treated with 4 parts by mass of γ-methacryloyloxypropyltrimethoxysilane by a conventional method. Thus, a silane-treated silica powder was obtained.
Inorganic filler 4: Silane-treated barium glass powder
Barium glass (manufactured by Esstech, Inc. under the product code "E-3000") was ground in a ball mill to obtain a barium glass powder. The average particle diameter of the barium glass powder thus obtained was measured using a laser diffraction particle size distribution analyzer (manufactured by Shimadzu Corporation, Model "SALD-2100"). The average particle diameter was 2.4 µm. 100 parts by mass of this barium glass powder was surface-treated with 3 parts by mass of γ-methacryloyloxypropyltrimethoxysilane by a conventional method. Thus, a silane-treated barium glass powder was obtained.

[Others]
BHT: 2,6-di-t-butyl-4-methylphenol (stabilizer (polymerization inhibitor))
[Example 1 and Comparative Example 1 Employment of Non-Solvent Dental Adhesive Composition for Dental Bonding Material]

Examples 1-1 to 1-16 and Comparative Examples 1-1 to 1-5

Dental bonding materials of Examples 1-1 to 1-16 and Comparative Examples 1-1 to 1-5 were prepared with the use of the above components by mixing and dispersing the components described in Tables 1 and 2 at ordinary temperature. Then, the tensile bond strength to dentin and the dentin cohesive failure rate were measured according to the methods described below for the dental bonding materials obtained. Tables 1 and 2 show the contents (parts by mass) of the components of the dental bonding materials of Examples and Comparative Examples and the test results for Examples and Comparative Examples.

[Tensile Bond Strength to Wet Dentin]
The labial surfaces of bovine mandibular incisors were each ground with #80 silicon carbide paper (manufactured by Nihon Kenshi Co., Ltd.) under running water to obtain samples with an exposed flat dentin surface. Each of the obtained samples was further ground with #1000 silicon carbide paper (manufactured by Nihon Kenshi Co., Ltd.) under running water. After the completion of grinding, each sample was dried by removing water from its surface by air-blowing. To the dried smooth surface was attached an about 150-µm-thick adhesive tape having a circular hole of 3-mm diameter, so that an adhesive area was defined. To the adherent surface in the circular hole was applied water-soaked absorbent cotton to form a gloss layer of water.

Each of the dental bonding materials prepared in Examples and Comparative Examples was applied within the circular hole with a brush and left for 10 seconds, after which the surface was air-blown. Subsequently, the applied dental bonding material was cured by 10-second light irradiation using a dental LED light irradiation device (manufactured by ULATRADENT PRODUCTS, INC. under the trade name "VALO").

A dental filling composite resin (manufactured by KURARAY NORITAKE DENTAL INC. under the trade name "CLEARFIL AP-X" (registered trademark)) was applied to the surface of the obtained cured product of the dental bonding material, which was covered with a release film (made of polyester). Next, a glass slide was placed on and pressed against the release film to flatten the surface of the applied composite resin. Subsequently, the applied composite resin was cured by 20-second light irradiation through the release film using the irradiation device ("VALO").

To the surface of the obtained cured product of the dental filling composite resin was adhered an end face (circular cross section) of a cylindrical stainless steel rod (diameter: 7 mm, length: 2.5 cm) using a commercially-available dental resin cement (manufactured by Kuraray Noritake Dental Inc. under the trade name "PANAVIA 21"). After the adhesion, the sample was left to stand at room temperature for 30 minutes and then immersed in distilled water to obtain an adhesion test sample. There were produced 20 such adhesion test samples. All samples immersed in distilled water were left to stand in a thermostat maintained at 37° C. for 24 hours. To evaluate the initial bond strength, 10 out of the 20 samples were measured for their tensile bond strength immediately after left to stand for 24 hours. To evaluate the bond durability, the remaining 10 samples were further subjected to 4000 cycles of thermal cycling one cycle of which consists of immersion in 4° C. cold water and 60° C. hot water for 1 minute each, and then measured for the tensile bond strength.

The tensile bond strength of the adhesion test samples was measured using a universal testing machine (manufactured by Shimadzu Corporation) with a crosshead speed set at 2 mm/minute. The average was defined as the tensile bond strength.

[Dentin Cohesive Failure Rate]

A fracture surface of each of the adhesion test samples having been subjected to the tensile bond strength measurement for the initial bond strength and the bond durability was visually observed after the test. The proportion (%) of samples whose dentin part was broken to the total number of the samples was defined as the dentin cohesive failure rate. A high dentin cohesive failure rate means that the polymerization curability of the adhesive interface portion and that of the inside of the resin-impregnated layer are high and the bonding condition at the adhesive interface portion is good.

TABLE 1

| Component (parts by mass) | | Ex. 1-1 | Ex. 1-2 | Ex. 1-3 | Ex. 1-4 | Ex. 1-5 | Ex. 1-6 | Ex. 1-7 | Ex. 1-8 | Ex. 1-9 | Ex. 1-10 | Ex. 1-11 | Ex. 1-12 | Ex. 1-13 |
|---|---|---|---|---|---|---|---|---|---|---|---|---|---|---|
| Acid group-containing polymerizable monomer (A) | MDP | 10 | 10 | 10 | 10 | 10 | 10 | 10 | 10 | 10 | 10 | 10 | 10 | 10 |
| Hydrophobic polymerizable monomer (B) having no acid group | Bis-GMA | 30 | 30 | 30 | 30 | 30 | 30 | 30 | 30 | 30 | 30 | 30 | 30 | 30 |
| Hydrophilic polymerizable monomer (D) having no acid group | HEMA | 30 | 30 | 30 | 30 | 30 | 30 | 30 | 30 | 30 | 30 | — | 30 | 30 |
| | DEAA | — | — | — | — | — | — | — | — | — | — | 30 | — | — |
| Water-soluble photopolymerization initiator (C) | Li-TPO | 0.1 | 0.3 | 0.5 | 1 | — | — | — | — | — | — | — | 0.5 | — |
| | Na-TPO | — | — | — | — | 0.5 | — | — | — | — | — | — | — | — |
| | BAPO-OLi | — | — | — | — | — | 0.5 | — | — | — | — | — | — | — |
| | BAPO-ONa | — | — | — | — | — | — | 0.1 | 0.3 | 0.5 | 1 | 0.5 | — | 0.5 |
| Water-insoluble photopolymerization initiator (E) | CQ | 1 | 1 | 1 | 1 | 1 | 1 | 1 | 1 | 1 | 1 | 1 | 1 | 1 |
| | TMDPO | — | — | — | — | — | — | — | — | — | — | — | — | 0.5 |
| Polymerization accelerator (F) | DABE | 2 | 2 | 2 | 2 | 2 | 2 | 2 | 2 | 2 | 2 | 2 | 2 | 2 |
| Polymerization inhibitor | BHT | 0.05 | 0.05 | 0.05 | 0.05 | 0.05 | 0.05 | 0.05 | 0.05 | 0.05 | 0.05 | 0.05 | 0.05 | 0.05 |
| Filler (G) | Inorganic filler 1 | 1 | 1 | 1 | 1 | 1 | 1 | 1 | 1 | 1 | 1 | 1 | — | 1 |
| Tensile bond strength (MPa) to wet dentin | Initial bond strength | 18.4 | 18.8 | 19.3 | 18.5 | 17.7 | 19.1 | 18.2 | 18.6 | 19.5 | 18.3 | 19.0 | 19.2 | 19.6 |
| | Bond durability | 16.4 | 16.7 | 17.1 | 16.6 | 16.3 | 16.6 | 16.1 | 16.7 | 17.3 | 16.5 | 16.9 | 16.8 | 17.9 |
| Dentin cohesive failure rate (%) | Initial bond strength | 80 | 80 | 90 | 80 | 70 | 80 | 80 | 80 | 80 | 80 | 70 | 80 | 90 |
| | Bond durability | 70 | 80 | 90 | 70 | 60 | 70 | 70 | 70 | 80 | 70 | 60 | 70 | 80 |

TABLE 2

| Component (parts by mass) | | Ex. 1-14 | Ex. 1-15 | Ex. 1-16 | Com. Ex. 1-1 | Com. Ex. 1-2 | Com. Ex. 1-3 | Com. Ex. 1-4 | Com. Ex. 1-5 |
|---|---|---|---|---|---|---|---|---|---|
| Acid group-containing polymerizable monomer (A) | MDP | 10 | 10 | 10 | 10 | 10 | 10 | 10 | 10 |
| Hydrophobic polymerizable monomer (B) having no acid group | Bis-GMA | 30 | 30 | 30 | 30 | 30 | 30 | 30 | 30 |

TABLE 2-continued

| Component (parts by mass) | | Ex. 1-14 | Ex. 1-15 | Ex. 1-16 | Com. Ex. 1-1 | Com. Ex. 1-2 | Com. Ex. 1-3 | Com. Ex. 1-4 | Com. Ex. 1-5 |
|---|---|---|---|---|---|---|---|---|---|
| Hydrophilic polymerizable monomer (D) having no acid group | HEMA | 30 | 30 | 30 | 30 | 30 | 30 | 30 | 30 |
| Water-soluble photopolymerization initiator (C) | Li-TPO | — | 1.2 | 1.2 | — | — | — | — | — |
| | BAPO-ONa | 0.5 | — | — | — | — | — | — | — |
| Water-insoluble photopolymerization initiator (E) | CQ | 1 | 0.2 | — | 1 | 1 | 1 | 1 | 1 |
| | TMDPO | — | — | — | — | 0.5 | — | — | — |
| | BAPO | 0.5 | — | — | — | — | 0.5 | — | — |
| | TMDPO-A1 | — | — | — | — | — | — | 0.5 | — |
| | BAPO-A1 | — | — | — | — | — | — | — | 0.5 |
| Polymerization accelerator (F) | DABE | 2 | 2 | — | 2 | 2 | 2 | 2 | 2 |
| Polymerization inhibitor | BHT | 0.05 | 0.05 | 0.05 | 0.05 | 0.05 | 0.05 | 0.05 | 0.05 |
| Filler (G) | Inorganic filler 1 | 1 | 1 | 1 | 1 | 1 | 1 | 1 | 1 |
| Tensile bond strength (MPa) to wet dentin | Initial bond strength | 19.8 | 17.0 | 15.0 | 10.3 | 10.6 | 10.8 | 10.4 | 10.8 |
| | Bond durability | 18.4 | 16.1 | 13.6 | 8.1 | 8.8 | 8.4 | 7.7 | 8.2 |
| Dentin cohesive failure rate (%) | Initial bond strength | 90 | 70 | 50 | 0 | 10 | 0 | 0 | 10 |
| | Bond durability | 90 | 60 | 40 | 0 | 0 | 0 | 0 | 0 |

As shown in Tables 1 and 2, the dental bonding materials (Examples 1-1 to 1-16) according to the present invention exhibited an initial bond strength of 15 MPa or more to dentin and a bond durability of 13 MPa or more to dentin. The dentin cohesive failure rates of the dental bonding materials according to the present invention were 50% or more for the samples having been measured for the initial bond strength and were 40% or more for the samples having been measured for the bond durability. It is suggested that the polymerization curability of the adhesive interface portion and that of the inside of the resin-impregnated layer were high. On the other hand, as shown in Table 2, the dental bonding materials (Comparative Examples 1-1 to 1-5) not including the water-soluble photopolymerization initiator (C) exhibited an initial bond strength of 11 MPa or less to dentin and a bond durability of 9 MPa or less to dentin. The dentin cohesive failure rates were 10% or less for the samples having been measured for the initial bond strength and were 0% for the samples having been measured for the bond durability. It is suggested that the polymerization curability of the adhesive interface portion and that of the inside of the resin-impregnated layer were insufficient.

[Examples 2 and Comparative Example 2 Employment of Non-Solvent Dental Adhesive Composition for Self-Adhesive Dental Composite Resin]

Examples 2-1 to 2-16 and Comparative Examples 2-1 to 2-5

Self-adhesive dental composite resins of Examples 2-1 to 2-16 and Comparative Examples 2-1 to 2-5 were prepared with the use of the above components by mixing and kneading the components described in Tables 3 and 4 at ordinary temperature. Then, the tensile bond strength to dentin was measured according to the method described below for these self-adhesive dental composite resins. Tables 3 and 4 show the contents (parts by mass) of the components of the self-adhesive dental composite resins of Examples and Comparative Examples and the test results for Examples and Comparative Examples.

[Tensile Bond Strength to Wet Dentin]

The labial surfaces of bovine mandibular incisors were each ground with #80 silicon carbide paper (manufactured by Nihon Kenshi Co., Ltd.) under running water to obtain samples with an exposed flat dentin surface. Each of the obtained samples was further ground with #1000 silicon carbide paper (manufactured by Nihon Kenshi Co., Ltd.) under running water. After the completion of grinding, each sample was dried by removing water from its surface by air-blowing. To the dried smooth surface was attached an about 150-μm-thick adhesive tape having a circular hole of 3-mm diameter, so that an adhesive area was defined. To the adherent surface in the circular hole was applied water-soaked absorbent cotton to form a gloss layer of water.

Each of the self-adhesive dental composite resins produced in Examples and Comparative Examples was applied within the circular hole, which was covered with a release film (made of polyester). Next, a glass slide was placed on and pressed against the release film to flatten the surface of the applied self-adhesive dental composite resin. Subsequently, the applied self-adhesive dental composite resin was cured by 10-second light irradiation through the release film using a dental LED light irradiation device (manufactured by ULATRADENT PRODUCTS, INC. under the trade name "VALO").

To the surface of the obtained cured product of the self-adhesive dental composite resin was adhered an end face (circular cross section) of a cylindrical stainless steel rod (diameter: 7 mm, length: 2.5 cm) using a commercially-available dental resin cement (manufactured by Kuraray Noritake Dental Inc. under the trade name "PANAVIA 21"). After the adhesion, the sample was left to stand at room temperature for 30 minutes and then immersed in distilled water to obtain an adhesion test sample. There were produced 20 such adhesion test samples. All samples immersed in distilled water were left to stand in a thermostat maintained at 37° C. for 24 hours. To evaluate the initial bond strength, 10 out of the 20 samples were measured for their tensile bond strength immediately after left to stand for 24 hours. To evaluate the bond durability, the remaining 10 samples were further subjected to 4000 cycles of thermal cycling one cycle of which consists of immersion in 4° C. cold water and 60° C. hot water for 1 minute each, and then measured for the tensile bond strength.

The tensile bond strength of the adhesion test samples was measured using a universal testing machine (manufactured by Shimadzu Corporation) with a crosshead speed set at 2 mm/minute. The average was defined as the tensile bond strength.

[Dentin Cohesive Failure Rate]

A fracture surface of each of the adhesion test samples having been subjected to the tensile bond strength measurement for the initial bond strength and the bond durability was visually observed after the test. The proportion (%) of samples whose dentin part was broken to the total number of the samples was defined as the dentin cohesive failure rate. A high dentin cohesive failure rate means that the polymerization curability of the adhesive interface portion and that of the inside of the resin-impregnated layer are high and the bonding condition at the adhesive interface portion is good.

TABLE 3

| Component (parts by mass) | | Ex. 2-1 | Ex. 2-2 | Ex. 2-3 | Ex. 2-4 | Ex. 2-5 | Ex. 2-6 | Ex. 2-7 |
|---|---|---|---|---|---|---|---|---|
| Acid group-containing polymerizable monomer (A) | MDP | 10 | 10 | 10 | 10 | 10 | 10 | 10 |
| Hydrophobic polymerizable monomer (B) having no acid group | Bis-GMA | 30 | 30 | 30 | 30 | 30 | 30 | 30 |
| | UDMA | — | — | — | — | — | — | — |
| | 3G | 30 | 30 | 30 | 30 | 30 | 30 | 30 |
| Hydrophilic polymerizable monomer (D) having no acid group | HEMA | 30 | 30 | 30 | 30 | 30 | 30 | 30 |
| | DEAA | — | — | — | — | — | — | — |
| Water-soluble photopolymerization initiator (C) | Li-TPO | 0.2 | 0.5 | 1 | — | — | — | — |
| | Na-TPO | — | — | — | 0.2 | — | — | — |
| | BAPO-OLi | — | — | — | — | 0.2 | — | — |
| | BAPO-ONa | — | — | — | — | — | 0.2 | 0.5 |
| Water-insoluble photopolymerization initiator (E) | CQ | 0.2 | 0.2 | 0.2 | 0.2 | 0.2 | 0.2 | 0.2 |
| | TMDPO | — | — | — | — | — | — | — |
| Polymerization accelerator (F) | DABE | 0.4 | 0.4 | 0.4 | 0.4 | 0.4 | 0.4 | 0.4 |
| Polymerization inhibitor | BHT | 0.05 | 0.05 | 0.05 | 0.05 | 0.05 | 0.05 | 0.05 |
| Filler (G) | Inorganic filler 2 | 20 | 20 | 20 | 20 | 20 | 20 | 20 |
| | Inorganic filler 3 | 280 | 280 | 280 | 280 | 280 | 280 | 280 |
| | Inorganic filler 4 | — | — | — | — | — | — | — |
| Tensile bond strength (MPa) to wet dentin | Initial bond strength | 15.6 | 16.1 | 15.5 | 15.3 | 16.4 | 16.8 | 16.3 |
| | Bond durability | 15.3 | 15.6 | 14.3 | 14.1 | 14.8 | 15.7 | 15.4 |
| Dentin cohesive failure rate (%) | Initial bond strength | 60 | 60 | 60 | 60 | 60 | 70 | 70 |
| | Bond durability | 50 | 60 | 50 | 50 | 50 | 70 | 60 |

| Component (parts by mass) | | Ex. 2-8 | Ex. 2-9 | Ex. 2-10 | Ex. 2-11 | Ex. 2-12 |
|---|---|---|---|---|---|---|
| Acid group-containing polymerizable monomer (A) | MDP | 10 | 10 | 10 | 10 | 10 |
| Hydrophobic polymerizable monomer (B) having no acid group | Bis-GMA | 30 | 10 | 10 | 10 | 10 |
| | UDMA | — | 20 | 20 | 20 | 20 |
| | 3G | 30 | 30 | 30 | 30 | 30 |
| Hydrophilic polymerizable monomer (D) having no acid group | HEMA | 30 | 30 | — | 30 | 30 |
| | DEAA | — | — | 30 | — | — |
| Water-soluble photopolymerization initiator (C) | Li-TPO | — | 0.2 | — | 0.2 | — |
| | Na-TPO | — | — | — | — | — |
| | BAPO-OLi | — | — | — | — | — |
| | BAPO-ONa | 1 | — | 0.2 | — | 0.2 |
| Water-insoluble photopolymerization initiator (E) | CQ | 0.2 | 0.2 | 0.2 | 0.2 | 0.2 |
| | TMDPO | — | — | — | — | 0.5 |
| Polymerization accelerator (F) | DABE | 0.4 | 0.4 | 0.4 | 0.4 | 0.4 |
| Polymerization inhibitor | BHT | 0.05 | 0.05 | 0.05 | 0.05 | 0.05 |
| Filler (G) | Inorganic filler 2 | 20 | 20 | 20 | 20 | 20 |
| | Inorganic filler 3 | 280 | 280 | 280 | — | 280 |
| | Inorganic filler 4 | — | — | — | 280 | — |

TABLE 3-continued

| | | | | | | |
|---|---|---|---|---|---|---|
| Tensile bond strength (MPa) to wet dentin | Initial bond strength | 15.7 | 16.7 | 16.3 | 15.7 | 16.9 |
| | Bond durability | 14.8 | 16.4 | 15.5 | 14.9 | 16.2 |
| Dentin cohesive failure rate (%) | Initial bond strength | 60 | 70 | 60 | 60 | 70 |
| | Bond durability | 60 | 70 | 50 | 60 | 60 |

TABLE 4

| Component (parts by mass) | | Ex. 2-13 | Ex. 2-14 | Ex. 2-15 | Ex. 2-16 | Com. Ex. 2-1 | Com. Ex. 2-2 | Com. Ex. 2-3 | Com. Ex. 2-4 | Com. Ex. 2-5 |
|---|---|---|---|---|---|---|---|---|---|---|
| Acid group-containing polymerizable monomer (A) | MDP | 10 | 10 | 10 | 10 | 10 | 10 | 10 | 10 | 10 |
| Hydrophobic polymerizable monomer (B) having no acid group | Bis-GMA | 10 | 10 | 10 | 10 | 10 | 10 | 10 | 10 | 10 |
| | UDMA | 20 | 20 | 20 | 20 | 20 | 20 | 20 | 20 | 20 |
| | 3G | 30 | 30 | 30 | 30 | 30 | 30 | 30 | 30 | 30 |
| Hydrophilic polymerizable monomer (D) having no acid group | HEMA | 30 | 30 | 30 | 30 | 30 | 30 | 30 | 30 | 30 |
| Water-soluble photopolymerization initiator (C) | Li-TPO | — | — | 1 | 1 | — | — | — | — | — |
| | BAPO-ONa | 0.2 | 0.1 | — | — | — | — | — | — | — |
| Water-insoluble photopolymerization initiator (E) | CQ | 0.2 | 0.4 | 0.1 | — | 0.2 | 0.2 | 0.2 | 0.2 | 0.2 |
| | TMDPO | — | — | — | — | — | 0.5 | — | — | — |
| | BAPO | 0.5 | 0.5 | — | — | — | — | 0.5 | — | — |
| | TMDPO-A1 | — | — | — | — | — | — | — | 0.5 | — |
| | BAPO-A1 | — | — | — | — | — | — | — | — | 0.5 |
| Polymerization accelerator (F) | DABE | 0.4 | 0.4 | 0.4 | — | 0.4 | 0.4 | 0.4 | 0.4 | 0.4 |
| Others | BHT | 0.05 | 0.05 | 0.05 | 0.05 | 0.05 | 0.05 | 0.05 | 0.05 | 0.05 |
| Filler (G) | Inorganic filler 2 | 20 | 20 | 20 | 20 | 20 | 20 | 20 | 20 | 20 |
| | Inorganic filler 3 | 280 | 280 | 280 | 280 | 280 | 280 | 280 | 280 | 280 |
| Tensile bond strength (MPa) to wet dentin | Initial bond strength | 17.1 | 17.2 | 15.4 | 13.0 | 6.3 | 6.5 | 6.6 | 5.8 | 6.7 |
| | Bond durability | 16.5 | 16.5 | 14.3 | 12.1 | 4.9 | 4.8 | 5.1 | 4.3 | 4.5 |
| Dentin cohesive failure rate (%) | Initial bond strength | 70 | 70 | 70 | 40 | 0 | 0 | 0 | 0 | 0 |
| | Bond durability | 70 | 70 | 60 | 30 | 0 | 0 | 0 | 0 | 0 |

As shown in Tables 3 and 4, the self-adhesive dental composite resins (Examples 2-1 to 2-16) according to the present invention exhibited an initial bond strength of 13 MPa or more to dentin and a bond durability of 12 MPa or more to dentin. The dentin cohesive failure rates of the self-adhesive dental composite resins according to the present invention were 40% or more for the samples having been measured for the initial bond strength and were 30% or more for the samples having been measured for the bond durability. It is suggested that the polymerization curability of the adhesive interface portion and that of the inside of the resin-impregnated layer were high. On the other hand, as shown in Table 4, the self-adhesive dental composite resins (Comparative Examples 2-1 to 2-5) not including the water-soluble photopolymerization initiator (C) exhibited an initial bond strength of 7 MPa or less to dentin and a bond durability of 6 MPa or less to dentin. The dentin cohesive failure rates were 0% for the samples having been measured for the initial bond strength and the samples having been measured for the bond durability. It is suggested that the polymerization curability of the adhesive interface portion and that of the inside of the resin-impregnated layer were insufficient.

[Examples 3 and Comparative Example 3 Employment of Non-Solvent Dental Adhesive Composition for Dental Bonding Material]

Examples 3-1 to 3-14 and Comparative Examples 3-1 to 3-5

Dental bonding materials of Examples 3-1 to 3-14 and Comparative Examples 3-1 to 3-5 were prepared with the use of the above components by mixing and dispersing the components described in Table 5 at ordinary temperature. Then, the tensile bond strength to dentin was measured according to the method described below for the dental bonding materials obtained. Table 5 shows the contents (parts by mass) of the components of the dental bonding materials of Examples and Comparative Examples and the test results for Examples and Comparative Examples.

[Tensile Bond Strength to Dry Dentin]

The labial surfaces of bovine mandibular incisors were each ground with #80 silicon carbide paper (manufactured by Nihon Kenshi Co., Ltd.) under running water to obtain samples with an exposed flat dentin surface. Each of the obtained samples was further ground with #1000 silicon carbide paper (manufactured by Nihon Kenshi Co., Ltd.) under running water. After the completion of grinding, each sample was dried by removing water from its surface by air-blowing. To the dried smooth surface was attached an about 150-μm-thick adhesive tape having a circular hole of 3-mm diameter, so that an adhesive area was defined.

Each of the dental bonding materials prepared in Examples and Comparative Examples was applied within the circular hole with a brush and left for 10 seconds, after which the surface was air-blown. Subsequently, the applied dental bonding material was cured by 10-second light irradiation using a dental LED light irradiation device (manufactured by Morita Corporation under the trade name "Pencure 2000").

A dental filling composite resin (manufactured by KURARAY NORITAKE DENTAL INC. under the trade name "CLEARFIL AP-X" (registered trademark)) was applied to the surface of the obtained cured product of the dental bonding material, which was covered with a release film (made of polyester). Next, a glass slide was placed on and pressed against the release film to flatten the surface of the applied composite resin. Subsequently, the applied composite resin was cured by 20-second light irradiation through the release film using the irradiation device ("Pencure 2000").

To the surface of the obtained cured product of the dental filling composite resin was adhered an end face (circular cross section) of a cylindrical stainless steel rod (diameter: 7 mm, length: 2.5 cm) using a commercially-available dental resin cement (manufactured by Kuraray Noritake Dental Inc. under the trade name "PANAVIA 21"). After the adhesion, the sample was left to stand at room temperature for 30 minutes and then immersed in distilled water to obtain an adhesion test sample. There were produced 20 such adhesion test samples. All samples immersed in distilled water were left to stand in a thermostat maintained at 37° C. for 24 hours. To evaluate the initial bond strength, 10 out of the 20 samples were measured for their tensile bond strength immediately after left to stand for 24 hours. To evaluate the bond durability, the remaining 10 samples were further subjected to 4000 cycles of thermal cycling one cycle of which consists of immersion in 4° C. cold water and 60° C. hot water for 1 minute each, and then measured for the tensile bond strength.

The tensile bond strength of the adhesion test samples was measured using a universal testing machine (manufactured by Shimadzu Corporation) with a crosshead speed set at 2 mm/minute. The average was defined as the tensile bond strength.

[Dentin Cohesive Failure Rate]

A fracture surface of each of the adhesion test samples having been subjected to the tensile bond strength measurement for the initial bond strength and the bond durability was visually observed after the test. The proportion (%) of samples whose dentin part was broken to the total number of the samples was defined as the dentin cohesive failure rate. A high dentin cohesive failure rate means that the polymerization curability of the adhesive interface portion and that of the inside of the resin-impregnated layer are high and the bonding condition at the adhesive interface portion is good.

TABLE 5

| Component (parts by mass) | | Ex. 3-1 | Ex. 3-2 | Ex. 3-3 | Ex. 3-4 | Ex. 3-5 | Ex. 3-6 | Ex. 3-7 | Ex. 3-8 | Ex. 3-9 | Ex. 3-10 |
|---|---|---|---|---|---|---|---|---|---|---|---|
| Acid group-containing polymerizable monomer (A) | MDP | 3 | 3 | 3 | 3 | 3 | 3 | 3 | 3 | 3 | 3 |
| Hydrophobic polymerizable monomer (B) having no acid group | DD | 75.4 | 75.4 | 75.4 | 75.4 | 75.4 | 95 | 75.4 | 75.4 | 75.4 | 75.4 |
| | MAEA | 10.1 | 14.8 | 14.8 | 14.8 | 19.6 | — | 19.6 | 19.6 | 19.6 | 14.8 |
| Hydrophilic polymerizable monomer (D) having no acid group | HEMA | 9.5 | 4.8 | 4.8 | 4.8 | — | — | — | — | — | — |
| | DEAA | — | — | — | — | — | — | — | — | — | 4.8 |
| Water-soluble photopolymerization initiator (C) | BAPO-ONa | 0.5 | 0.3 | 0.5 | 1 | 0.5 | 0.5 | — | — | — | 0.5 |
| | BAPO-OLi | — | — | — | — | — | — | 0.5 | — | — | — |
| | Na-TPO | — | — | — | — | — | — | — | 0.5 | — | — |
| | Li-TPO | — | — | — | — | — | — | — | — | 0.5 | — |
| Water-insoluble photopolymerization initiator (E) | CQ | 0.6 | 0.6 | 0.6 | 0.6 | 0.6 | 0.6 | 0.6 | 0.6 | 0.6 | 0.6 |
| | TMDPO | — | — | — | — | — | — | — | — | — | — |
| | BAPO | — | — | — | — | — | — | — | — | — | — |
| | TMDPO-A1 | — | — | — | — | — | — | — | — | — | — |
| | BAPO-A1 | — | — | — | — | — | — | — | — | — | — |
| Polymerization accelerator (F) | DABE | 0.8 | 0.8 | 0.8 | 0.8 | 0.8 | 0.8 | 0.8 | 0.8 | 0.8 | 0.8 |
| Others | BHT | 0.1 | 0.1 | 0.1 | 0.1 | 0.1 | 0.1 | 0.1 | 0.1 | 0.1 | 0.1 |
| Filler (G) | Inorganic filler 1 | — | — | — | — | — | — | — | — | — | — |
| Tensile bond strength (MPa) to dry dentin | Initial bond strength | 16.4 | 17.1 | 18.8 | 17.8 | 17.9 | 16.9 | 17.5 | 17.3 | 17.4 | 16.3 |
| | Bond durability | 14.2 | 15.6 | 15.8 | 15.8 | 16.2 | 14.8 | 16.0 | 15.5 | 15.8 | 14.4 |
| Dentin cohesive failure rate (%) | Initial bond strength | 80 | 80 | 80 | 70 | 70 | 70 | 80 | 80 | 80 | 70 |
| | Bond durability | 60 | 70 | 80 | 70 | 70 | 60 | 70 | 70 | 70 | 60 |

TABLE 5-continued

| Component (parts by mass) | | Ex. 3-11 | Ex. 3-12 | Ex. 3-13 | Ex. 3-14 | Com. Ex. 3-1 | Com. Ex. 3-2 | Com. Ex. 3-3 | Com. Ex. 3-4 | Com. Ex. 3-5 |
|---|---|---|---|---|---|---|---|---|---|---|
| Acid group-containing polymerizable monomer (A) | MDP | 3 | 3 | 3 | 3 | 3 | 3 | 3 | 3 | 3 |
| Hydrophobic polymerizable monomer (B) having no acid group | DD | 75.4 | 75.4 | 61.2 | 42.2 | 75.4 | 75.4 | 75.4 | 75.4 | 75.4 |
| | MAEA | 19.6 | 14.8 | 14.8 | 5.3 | 19.6 | 19.6 | 19.6 | 19.6 | 19.6 |
| Hydrophilic polymerizable monomer (D) having no acid group | HEMA | — | 4.8 | 19 | 47.5 | — | — | — | — | — |
| | DEAA | — | — | — | — | — | — | — | — | — |
| Water-soluble photopolymerization initiator (C) | BAPO-ONa | 0.5 | 0.5 | 0.5 | 0.5 | — | — | — | — | — |
| | BAPO-OLi | — | — | — | — | — | — | — | — | — |
| | Na-TPO | — | — | — | — | — | — | — | — | — |
| | Li-TPO | — | — | — | — | — | — | — | — | — |
| Water-insoluble photopolymerization initiator (E) | CQ | 0.3 | 0.6 | 0.6 | 0.6 | 0.8 | 0.6 | 0.6 | 0.6 | 0.6 |
| | TMDPO | — | — | — | — | — | 0.5 | — | — | — |
| | BAPO | 0.3 | — | — | — | — | — | 0.5 | — | — |
| | TMDPO-Al | — | — | — | — | — | — | — | 0.5 | — |
| | BAPO-Al | — | — | — | — | — | — | — | — | 0.5 |
| Polymerization accelerator (F) | DABE | 0.8 | 0.8 | 0.8 | 0.8 | 1.1 | 0.8 | 0.8 | 0.8 | 0.8 |
| Others | BHT | 0.1 | 0.1 | 0.1 | 0.1 | 0.1 | 0.1 | 0.1 | 0.1 | 0.1 |
| Filler (G) | Inorganic filler 1 | — | 3 | — | — | — | — | — | — | — |
| Tensile bond strength (MPa) to dry dentin | Initial bond strength | 18.0 | 18.9 | 13.8 | 14.2 | 10.3 | 10.6 | 10.4 | 10.8 | 10.6 |
| | Bond durability | 15.6 | 16.0 | 13.5 | 13.6 | 8.5 | 7.7 | 8.2 | 8.1 | 8.8 |
| Dentin cohesive failure rate (%) | Initial bond strength | 80 | 80 | 60 | 50 | 0 | 10 | 0 | 0 | 0 |
| | Bond durability | 70 | 70 | 50 | 40 | 0 | 0 | 0 | 0 | 0 |

As shown in Table 5, the dental bonding materials (Examples 3-1 to 3-14) according to the present invention exhibited an initial bond strength of 13 MPa or more to dried dentin and a bond durability of 13 MPa or more to dried dentin. The dentin cohesive failure rates of the dental bonding materials according to the present invention were 50% or more for the samples having been measured for the initial bond strength and were 40% or more for the samples having been measured for the bond durability. It is suggested that the polymerization curability of the adhesive interface portion and that of the inside of the resin-impregnated layer were high. On the other hand, as shown in Table 5, the dental bonding materials (Comparative Examples 3-1 to 3-5) not including the water-soluble photopolymerization initiator (C) exhibited an initial bond strength of less than 11 MPa to dentin and a bond durability of less than 9 MPa to dentin. The dentin cohesive failure rates were 10% or less for the samples having been measured for the initial bond strength and were 0% for the samples having been measured for the bond durability. It is suggested that the polymerization curability of the adhesive interface portion and that of the inside of the resin-impregnated layer were insufficient.

[Examples 4 and Comparative Example 4 Employment of Non-Solvent Dental Adhesive Composition for Self-Adhesive Dental Composite Resin]

Examples 4-1 to 4-13 and Comparative Examples 4-1 to 4-5

Self-adhesive dental composite resins of Examples 4-1 to 4-13 and Comparative Examples 4-1 to 4-5 were prepared with the use of the above components by mixing and kneading the components described in Table 2 at ordinary temperature. Then, the tensile bond strength to dentin was measured according to the method described below for these self-adhesive dental composite resins. Table 6 shows the contents (parts by mass) of the components of the self-adhesive dental composite resins of Examples and Comparative Examples and the test results for Examples and Comparative Examples.

[Tensile Bond Strength to Dry Dentin]

The labial surfaces of bovine mandibular incisors were each ground with #80 silicon carbide paper (manufactured by Nihon Kenshi Co., Ltd.) under running water to obtain samples with an exposed flat dentin surface. Each of the obtained samples was further ground with #1000 silicon carbide paper (manufactured by Nihon Kenshi Co., Ltd.) under running water. After the completion of grinding, each sample was dried by removing water from its surface by air-blowing. To the dried smooth surface was attached an about 150-μm-thick adhesive tape having a circular hole of 3-mm diameter, so that an adhesive area was defined.

Each of the self-adhesive dental composite resins produced in Examples and Comparative Examples was applied within the circular hole, which was covered with a release film (made of polyester). Next, a glass slide was placed on and pressed against the release film to flatten the surface of the applied self-adhesive dental composite resin. After left for 10 seconds, the applied self-adhesive dental composite resin was cured by 10-second light irradiation through the release film using a dental LED light irradiation device (manufactured by Morita Corporation under the trade name "Pencure 2000").

To the surface of the obtained cured product of the self-adhesive dental composite resin was adhered an end face (circular cross section) of a cylindrical stainless steel rod (diameter: 7 mm, length: 2.5 cm) using a commercially-available dental resin cement (manufactured by Kuraray Noritake Dental Inc. under the trade name "PANAVIA 21"). After the adhesion, the sample was left to stand at room temperature for 30 minutes and then immersed in distilled water to obtain an adhesion test sample. There were produced 20 such adhesion test samples. All samples immersed in distilled water were left to stand in a thermostat maintained at 37° C. for 24 hours. To evaluate the initial bond strength, 10 out of the 20 samples were measured for their tensile bond strength immediately after left to stand for 24 hours. To evaluate the bond durability, the remaining 10 samples were further subjected to 4000 cycles of thermal cycling one cycle of which consists of immersion in 4° C. cold water and 60° C. hot water for 1 minute each, and then measured for the tensile bond strength.

The tensile bond strength of the adhesion test samples was measured using a universal testing machine (manufactured by Shimadzu Corporation) with a crosshead speed set at 2 mm/minute. The average was defined as the tensile bond strength.

[Dentin Cohesive Failure Rate]

A fracture surface of each of the adhesion test samples having been subjected to the tensile bond strength measurement for the initial bond strength and the bond durability was visually observed after the test. The proportion (%) of samples whose dentin part was broken to the total number of the samples was defined as the dentin cohesive failure rate. A high dentin cohesive failure rate means that the polymerization curability of the adhesive interface portion and that of the inside of the resin-impregnated layer are high and the bonding condition at the adhesive interface portion is good.

TABLE 6

| Component (parts by mass) | | Ex. 4-1 | Ex. 4-2 | Ex. 4-3 | Ex. 4-4 | Ex. 4-5 | Ex. 4-6 | Ex. 4-7 | Ex. 4-8 | Ex. 4-9 | Ex. 4-10 |
|---|---|---|---|---|---|---|---|---|---|---|---|
| Acid group-containing polymerizable monomer (A) | MDP | 10 | 10 | 10 | 10 | 10 | 10 | 10 | 10 | 10 | 10 |
| Hydrophobic polymerizable monomer (B) having no acid group | DD | 71.4 | 71.4 | 71.4 | 71.4 | 71.4 | 89.2 | 71.4 | 71.4 | 71.4 | 71.4 |
| | MAEA | 8.3 | 13.3 | 13.3 | 13.3 | 17.8 | — | 17.8 | 17.8 | 17.8 | 13.3 |
| Hydrophilic polymerizable monomer (D) having no acid group | HEMA | 8.9 | 4.5 | 4.5 | 4.5 | — | — | — | — | — | — |
| | DEAA | — | — | — | — | — | — | — | — | — | 4.5 |
| Water-soluble photopolymerization initiator (C) | BAPO-ONa | 0.2 | 0.1 | 0.2 | 0.5 | 0.2 | 0.2 | — | — | — | 0.2 |
| | BAPO-OLi | — | — | — | — | — | — | 0.2 | — | — | — |
| | Na-TPO | — | — | — | — | — | — | — | 0.2 | — | — |
| | Li-TPO | — | — | — | — | — | — | — | — | 0.2 | — |
| Water-insoluble photopolymerization initiator (E) | CQ | 0.2 | 0.2 | 0.2 | 0.2 | 0.2 | 0.2 | 0.2 | 0.2 | 0.2 | 0.2 |
| | TMDPO | — | — | — | — | — | — | — | — | — | — |
| | BAPO | — | — | — | — | — | — | — | — | — | — |
| | TMDPO-A1 | — | — | — | — | — | — | — | — | — | — |
| | BAPO-A1 | — | — | — | — | — | — | — | — | — | — |
| Polymerization accelerator (F) | DABE | 0.4 | 0.4 | 0.4 | 0.4 | 0.4 | 0.4 | 0.4 | 0.4 | 0.4 | 0.4 |
| Others | BHT | 0.05 | 0.05 | 0.05 | 0.05 | 0.05 | 0.05 | 0.05 | 0.05 | 0.05 | 0.05 |
| Filler (G) | Inorganic filler 2 | 20 | 20 | 20 | 20 | 20 | 20 | 20 | 20 | 20 | 20 |
| | Inorganic filler 3 | 280 | 280 | 280 | 280 | 280 | 280 | 280 | 280 | 280 | 280 |
| | Inorganic filler 4 | — | — | — | — | — | — | — | — | — | — |
| Tensile bond strength (MPa) to dry dentin | Initial bond strength | 13.5 | 15.1 | 15.6 | 15.3 | 14.8 | 13.8 | 14.6 | 14.7 | 14.5 | 13.0 |
| | Bond durability | 13.1 | 14.6 | 15.1 | 14.8 | 14.5 | 13.5 | 14.1 | 14.2 | 14.0 | 12.8 |
| Dentin cohesive failure rate (%) | Initial bond strength | 60 | 60 | 60 | 60 | 60 | 60 | 60 | 60 | 60 | 50 |
| | Bond durability | 40 | 60 | 60 | 60 | 60 | 40 | 50 | 50 | 50 | 50 |

| Component (parts by mass) | | Ex. 4-11 | Ex. 4-12 | Ex. 4-13 | Com. Ex. 4-1 | Com. Ex. 4-2 | Com. Ex. 4-3 | Com. Ex. 4-4 | Com. Ex. 4-5 |
|---|---|---|---|---|---|---|---|---|---|
| Acid group-containing polymerizable monomer (A) | MDP | 10 | 10 | 10 | 10 | 10 | 10 | 10 | 10 |
| Hydrophobic polymerizable monomer (B) having no acid group | DD | 71.4 | 71.4 | 58.7 | 71.4 | 71.4 | 71.4 | 71.4 | 71.4 |
| | MAEA | 17.8 | 17.8 | 13.3 | 17.8 | 17.8 | 17.8 | 17.8 | 17.8 |
| Hydrophilic polymerizable monomer (D) having no acid group | HEMA | — | — | 17.2 | — | — | — | — | — |
| | DEAA | — | — | — | — | — | — | — | — |
| Water-soluble photopolymerization | BAPO-ONa | 0.2 | 0.2 | 0.2 | — | — | — | — | — |
| | BAPO-OLi | | | | | | | | |

TABLE 6-continued

| | | | | | | | | | |
|---|---|---|---|---|---|---|---|---|---|
| initiator (C) | Na-TPO | — | — | — | — | — | — | — | — |
| | Li-TPO | — | — | — | — | — | — | — | — |
| Water-insoluble photopolymerization initiator (E) | CQ | 0.1 | 0.2 | 0.2 | 0.4 | 0.2 | 0.2 | 0.2 | 0.2 |
| | TMDPO | — | — | — | — | 0.2 | — | — | — |
| | BAPO | 0.1 | — | — | — | — | 0.2 | — | — |
| | TMDPO-A1 | — | — | — | — | — | — | 0.2 | — |
| | BAPO-A1 | — | — | — | — | — | — | — | 0.2 |
| Polymerization accelerator (F) | DABE | 0.4 | 0.4 | 0.4 | 0.4 | 0.4 | 0.4 | 0.4 | 0.4 |
| Others | BHT | 0.05 | 0.05 | 0.05 | 0.05 | 0.05 | 0.05 | 0.05 | 0.05 |
| Filler (G) | Inorganic filler 2 | 20 | 20 | 20 | 20 | 20 | 20 | 20 | 20 |
| | Inorganic filler 3 | 280 | | 280 | 280 | 280 | 280 | 280 | 280 |
| | Inorganic filler 4 | — | 280 | — | — | — | — | — | — |
| Tensile bond strength (MPa) to dry dentin | Initial bond strength | 15.2 | 14.9 | 11.8 | 6.5 | 6.6 | 5.8 | 6.7 | 6.3 |
| | Bond durability | 14.9 | 14.5 | 11.1 | 5.1 | 4.3 | 4.5 | 4.9 | 4.8 |
| Dentin cohesive failure rate (%) | Initial bond strength | 60 | 60 | 40 | 0 | 0 | 0 | 0 | 0 |
| | Bond durability | 60 | 50 | 30 | 0 | 0 | 0 | 0 | 0 |

As shown in Table 6, the self-adhesive dental composite resins (Examples 4-1 to 4-13) according to the present invention exhibited an initial bond strength of 11 MPa or more to dried dentin and a bond durability of 11 MPa or more to dried dentin. The dentin cohesive failure rates of the self-adhesive dental composite resins according to the present invention were 40% or more for the samples having been measured for the initial bond strength and were 30% or more for the samples having been measured for the bond durability. It is suggested that the polymerization curability of the adhesive interface portion and that of the inside of the resin-impregnated layer were high. On the other hand, as shown in Table 6, the self-adhesive dental composite resins (Comparative Examples 4-1 to 4-5) not including the water-soluble photopolymerization initiator (C) exhibited an initial bond strength of less than 7 MPa to dentin and a bond durability of less than 6 MPa to dentin. The dentin cohesive failure rates were 0% for the samples having been measured for the initial bond strength and the samples having been measured for the bond durability. It is suggested that the polymerization curability of the adhesive interface portion and that of the inside of the resin-impregnated layer were insufficient.

INDUSTRIAL APPLICABILITY

The non-solvent dental adhesive composition according to the present invention is suitably used as a dental bonding material, a self-adhesive dental composite resin, and a dental cement in the field of dentistry.

The invention claimed is:

1. A non-solvent dental adhesive composition, comprising:
    an acid group-containing polymerizable monomer (A);
    a hydrophobic polymerizable monomer (B) having no acid group; and
    a water-soluble photopolymerization initiator (C) having a solubility of 10 g/L or more in water at 25° C.,
    wherein the water-soluble photopolymerization initiator (C) is at least one selected from the group consisting of a compound represented by the following formula (1) and a compound represented by the following formula (2):

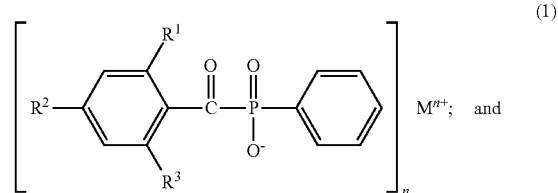

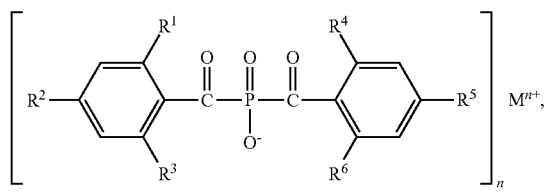

wherein $R^1$, $R^2$, $R^3$, $R^4$, $R^5$, and $R^6$ are each independently a linear or branched alkyl group comprising 1 to 4 carbon atoms or a halogen atom;

M is a hydrogen ion, an alkali metal ion, an alkaline-earth metal ion, a magnesium ion, a pyridinium ion comprising an optionally substituted pyridine ring, or an ammonium ion represented by $HN^+R^7R^8R^9$, wherein $R^7$, $R^8$, and $R^9$ are each independently an organic group or a hydrogen atom; and n represents 1 or 2.

2. The non-solvent dental adhesive composition of claim 1, further comprising a hydrophilic polymerizable monomer (D) having no acid group.

3. The non-solvent dental adhesive composition of claim 2, wherein a content of the hydrophilic polymerizable monomer (D) having no acid group with respect to a total mass of the hydrophobic polymerizable monomer (B) having no acid group and the hydrophilic polymerizable monomer (D) having no acid group is 50 mass % or less.

4. The non-solvent dental adhesive composition of claim 1, wherein the water-soluble photopolymerization initiator (C) comprises the compound represented by the formula (1).

5. The non-solvent dental adhesive composition of claim 1, wherein the acid group-containing polymerizable monomer (A) is a phosphate group-containing polymerizable monomer.

6. The non-solvent dental adhesive composition of claim 1, further comprising a water-insoluble photopolymerization initiator (E) having a solubility of less than 10 g/L in water at 25° C.

7. The non-solvent dental adhesive composition of claim 6, wherein a mass ratio between the water-soluble photopolymerization initiator (C) and the water-insoluble photopolymerization initiator (E) is 10:1 to 1:10.

8. A dental bonding material, comprising the non-solvent dental adhesive composition of claim 1.

9. A self-adhesive dental composite resin, comprising the non-solvent dental adhesive composition of claim 1.

10. A dental cement, comprising the non-solvent dental adhesive composition of claim 1.

11. The non-solvent dental adhesive composition of claim 1, wherein the water-soluble photopolymerization initiator (C) comprises the compound represented by the formula (2).

* * * * *